US007482018B2

(12) United States Patent
Soane et al.

(10) Patent No.: US 7,482,018 B2
(45) Date of Patent: Jan. 27, 2009

(54) USE OF OLIGOMERS AND POLYMERS FOR DRUG SOLUBILIZATION, STABILIZATION, AND DELIVERY

(75) Inventors: David S. Soane, Piedmont, CA (US); Daniel J. Suich, Oakland, CA (US)

(73) Assignees: Soane Family Trust, Piedmont, CA (US); Alexander Soane Annual Exclusion Trust, Piedmont, CA (US); Nicholas Soane Annual Exclusion Trust, Piedmont, CA (US)

( * ) Notice: Subject to any disclaimer, the term of this patent is extended or adjusted under 35 U.S.C. 154(b) by 946 days.

(21) Appl. No.: 10/328,898

(22) Filed: Dec. 23, 2002

(65) Prior Publication Data

US 2003/0180244 A1 Sep. 25, 2003

Related U.S. Application Data

(60) Provisional application No. 60/343,483, filed on Dec. 21, 2001.

(51) Int. Cl.
*A61K 9/10* (2006.01)
*C07K 2/00* (2006.01)
*C07K 5/107* (2006.01)

(52) U.S. Cl. ................................ 424/400; 514/2; 514/8; 530/300; 530/322; 530/345

(58) Field of Classification Search ....................... None
See application file for complete search history.

(56) References Cited

U.S. PATENT DOCUMENTS

| | | | |
|---|---|---|---|
| 4,002,531 | A | 1/1977 | Royer |
| 4,179,337 | A | 12/1979 | Davis et al. |
| 5,622,699 | A | 4/1997 | Rusoslahti et al. |
| 5,650,398 | A | 7/1997 | Kensil et al. |
| 5,804,604 | A | 9/1998 | Frankel et al. |
| 5,807,746 | A | 9/1998 | Lin et al. |
| 5,942,634 | A | 8/1999 | Siegel et al. |

(Continued)

FOREIGN PATENT DOCUMENTS

| | | |
|---|---|---|
| EP | 1 538 166 | 6/2005 |

(Continued)

OTHER PUBLICATIONS

Anderson et al. Folic acid-PEO-labeled liposomes to improve gastrointestinal absorption of encapsulated agents. Journal of Controlled Release. 1999, vol. 60, pp. 189-198.*

(Continued)

*Primary Examiner*—Jeffrey E Russel
(74) *Attorney, Agent, or Firm*—Nutter, McClennen & Fish, LLP

(57) ABSTRACT

The invention relates to the use of oligomers and polymers capable of rendering insoluble drugs soluble, protecting unstable drugs, and facilitating the delivery of drugs to their site of action. This invention further relates to processes for the preparation of such oligomers and polymers, and to compositions containing them. In some instances, surfactants, which can include an oligomer, polymer, small molecule, or other material, can be used to form a micelle for encapsulating the drug. The miscelle can be used to protect the drug until the drug is to be released.

44 Claims, 12 Drawing Sheets

U.S. PATENT DOCUMENTS

| | | | | |
|---|---|---|---|---|
| 6,143,917 | A * | 11/2000 | Harada et al. | 560/32 |
| 6,322,805 | B1 * | 11/2001 | Kim et al. | 424/426 |
| 6,365,146 | B1 | 4/2002 | Uhrich | 424/78.31 |
| 6,410,057 | B1 | 6/2002 | Kweon-Choi et al. | |
| 6,429,200 | B1 | 8/2002 | Monahan et al. | |
| 6,491,903 | B1 | 12/2002 | Forster et al. | |
| 6,492,560 | B2 * | 12/2002 | Wilbur et al. | 564/505 |
| 6,521,736 | B2 * | 2/2003 | Watterson et al. | 528/272 |
| 2001/0004454 | A1 * | 6/2001 | Wedeking et al. | 424/1.65 |
| 2001/0021703 | A1 * | 9/2001 | Kosak | 514/58 |
| 2002/0012680 | A1 * | 1/2002 | Patel et al. | 424/400 |
| 2002/0098999 | A1 | 7/2002 | Gallop et al. | |
| 2003/0176335 | A1 * | 9/2003 | Zhang et al. | 514/12 |
| 2006/0148728 | A1 * | 7/2006 | Lutz et al. | 514/27 |

FOREIGN PATENT DOCUMENTS

| | | |
|---|---|---|
| WO | WO 99/33940 | 7/1999 |
| WO | WO 99/65467 | 12/1999 |
| WO | WO 01/09163 | 2/2001 |
| WO | WO 01/47562 | 7/2001 |
| WO | WO 01/52826 | 7/2001 |
| WO | WO 01/62297 | 8/2001 |
| WO | WO 02/15877 | 2/2002 |
| WO | WO 02/19963 | 3/2002 |
| WO | WO 02/20033 | 3/2002 |
| WO | WO 02/49676 | 6/2002 |
| WO | WO 02/069930 | 9/2002 |

OTHER PUBLICATIONS

CRC Handbook of Chemistry and Physics, 79th ed., Lide ed., pp. 16-42-16-46, CRC Press (1998).

Fricker et al., Brit.J. Pharamacol. 117:217 (1996).

Yokoyama et al., "Preparation of Micelle-Forming Polymer-Drug Conjugates," Bioconjugate Chemistry, ACS, Washington, DC, 3(4):295-301 (1992).

Wiedmann, T. et al., "Examination of the Solubilization of Drugs by Bile Salt Micelles," J. Pharma. Sci. 91(8):1743-64 (Aug. 2002).

K. E. Anderson, et al., "*Formulation and Evaluation of a Folic Acid Receptor-Targeted Oral Vancomycin Liposomal Dosage Form*", Pharmaceutical Research, 2001, 18(3):316-322.

Annelise E. Baron et al., "*Bioinspired polymeric materials: in-between proteins and plastics*", Current Opinion in Chemical Biology, 1999, 3:681-687.

Nadya Belcheva, et al., "*Synthesis and Biological Activity of Polyethylene Glycol-Mouse Nerve Growth Factor Conjugate*", 1999, 10:932-937, Bioconjugate Chemistry.

Jonathan J. Burbaum et al., "*New technologies for high-throughput screening*", Current Opinion in Chemical Biology, 1997, 1:72-78.

Gerardo Byk et al., "*Synthesis, Activity, and Structure—Activity Relationship Studies of Novel Cationic Lipids for DNA Transfer*", J. Med. Chem, 1998, 41:224-235.

Duncan Q. M. Craig et al., "*Administration of Emulsions to the Gastrointestinal Tract*", Pharmaceutical emulsions and suspensions/ Gilberte Marti-Mestres, New York: Marcel Dekker, Inc., 2000, part 2, pp. 323-360.

Manisha P. Desai, et al., "*Gastrointestinal Uptake of Biodegradable Microparticles: Effect of Particle Size*", Pharmaceutical Research, 1996, 13(12):1838-1845.

Valerie Dodane, et al., "*Effect of chitosan an epithelial permeability and structure*", International Journal of Pharmaceutics, 1999, 182:21-32.

Fricker A. Fahr, et al., "*Permeation enhancement of octreotide by specific bile salts in rats and human subjects: in vitro, in vivo correlations*", British Journal of Pharmacology, 1996, 117, 217-223.

A. T. Florence, et al., "*Oral uptake and translocation of a polylysine dendrimer with a lipid surface*", Journal of Controlled Release, (2000) 65:253-259.

Sabine L. Flitsch, "*Chemical and enzymatic synthesis of glycopolymers*", Current Opinion in Chemical Biology, 2000, 4:619-625.

Koichi Fukase, "*Combinatorial and Solid-Phase Methods in Oligosaccharide Synthesis*", Glycoscience, 2001, 2:1621-1660.

Shiroh Futaki, et al., "*Arginine-rich Peptides*", The Journal of Biological Chemistry, 2001, 276(8):5836-5840.

Lino Gonzales, Jr. et al., "*Buried polar residues and structural specificity in the GCN4 leucine zipper*", Nature Structural Biology, 1996, 3(12):1011-1018.

Laxmikant Gharat, et al., "*Targeted drug delivery systems 6: Intracellular bioreductive activation, uptake and transport of an anticancer drug delivery system across intestinal Caco-2 cell monolayers*", International Journal of Pharmaceutics, 2001, 219:1-10.

Gilles Guichard, "*Solid-Phase Synthesis of Pseudopeptides and Oligomeric Peptide Backbone Mimetics*", Marcel Dekker, Inc., 2000, pp. 649-703.

Nasir Hussain, "*Ligand-mediated tissue specific drug delivery*", Advanced Drug Delivery Reviews, 2000, 43-95-100.

Constantia E. Kast et al., "*Thiolated polymers—thiomers: development and in vitro evaluation of chitosan-thioglycolic acid conjugates*", Biomaterials, 2001, 22:2345-2352.

Harold Koenig et al., "*Polyamines and $Ca^{2+}$ Mediate Hyperosmolal Opening of the Blood-Brain Barrier: In Vitro Studies in Isolated Rat Cerebral Capillaries*", Journal of Neurochemistry, 1989, 52(4):1135-1142.

Harold Koenig et al., "*Polyamines mediate the reversible opening of the blood-brain barrier by the intracarotid infusion of hyperosmolal mannitol*", Brain Research, 1989, 483:110-116.

Awie F. Kotze, et al., "*N-Trimethyl Chitosan Chloride as a Potential Absorption Enhancer Across Mucosal Surfaces: In Vitro Evaluation in Intstinal Epithelial Cells* (*Caco-2*)", Pharmaceutical Research, 1997, 14(9):1197-1202.

Werber Kramer, et al., "*Intestinal Absorption of Peptides by Coupling to Bile Acids*", The Journal of Biological Chemistry, 1994, 269(14):10621-10627.

G. Kwon, et al., "*Enhanced tumor accumulation and prolonged circulation times of micelle-forming poly* (*ethulene oxide-aspartate*) *block copolymer-adriamycin conjugates*", Journal of Controlled Release, 1994, 29:17-23.

Afsaneh Lavasanifar et al., "*Poly*(*ethylene oxide*)-*block-poly*(*L-amino acid*) *micelles for drug delivery*", Advanced Drug Delivery Reviews, 2002, 54:169-190.

George A. Lemieux, et al., "*Chemoselective ligation reactions with proteins,oligosaccharides and cells*", Trends Biotechnol., 1998, 16(12):506-513.

Karen J. MacGregor, et al., "*Influence of lipolysis on durg absorption from the gastro-intestinal tract*", Advanced Drug Delivery Reviews, 25(1997):33-46.

Hikaru Matsumoto, et al., "*Controlled Drug Release: New Water-Soluble Prodrugs of an HIV Protease Inhibitor*", Bioorganic & Medicinal Chemistry Letters, 2001, 11:605-609.

D.J. Mitchell, et al., "*Polyarginine enters cells more efficiently than other polycationic homopolymers*", J. Peptide Res., 2000,56:318-325.

Yuichiro Nakada, et al., "*The Effect of Additives on the Oral Mucosal Absorption of Human Calcitonin in Rats*", J. Pharmacobio-Dyn., 1988, 11:395-401.

Fredrik Nilsson, et al., "*The use of phage display for the development of tumour targeting agents*", Advanced Drug Delivery Reviews, 2000, 43:165-196.

Daniel W. Norbeck, et al., "*A Novel Prodrug of an Impermeant Inhibitor of 3-Deoxy-D-manno-2-octulosonate Cytidylyltransferase Has Antibacterial Activity*", J. Med. Chem., 1989, 32:625-629.

Peter H. Seeberger et al., "*Solid-Phase Oligosaccharide Sythesis and Combinatorial Carbohydrate Libraries*", Chem. Rev., 2000, 100:4349-4393.

Michael J. Soth, et al., "*Unnatural oligomers and unnatural oligomer libraries*", Current Opinion in Chemical Biology, 1997, 1:120-129.

Peter D. Senter, et al., "*Development of a Drug-Release Strategy Based on the Reductive Fragmentation of Benzyl Carbamate Disulfides*", J. Org. Chem., 1990, 55:2975-2978.

Tomomi Uchiyama, et al., "*Enhanced Permeability of Insulin across the Rat Intestinal Membrane by Various Absorption Enhancers:*

*Their Intestinal Mucosal Toxicity and Absorption-enhancing Mechanism of n-Lauryl-β-D-maltopyranoisde*", J. Pharm. Pharmacol., 1999, 51:1241-1250.

Paul A. Wender, et al., "*Oligocarbamate Molecular Transporters: Design, Synthesis, and Biological Evaluation of a New Class of Transporters for Drug Delivery*", J. Am Chem. Soc., 2002, 124:13382-13383.

Paul A. Wender et al., "*The design, synthesis, and evaluation of molecules that enable or enhance cellular uptake: Peptoid molecular transporters*", PNAS, 2000, 97(24):13003-13008.

Yuji Yamamoto, et al., "*Long-circulating poly(ethylene glycol)-poly (D,L-lactide) block copolymer micelles with modulated surface charge*", Journal of Controlled Release, 2001, 77:27-38.

Joseph Zabner, "*Cationic lipids used in gene transfer*", Advanced Drug Delivery Reviews, 1997, 27:17-28.

Samuel Zalipsky, "*Functionalized Poly(ethylene glycol) for Preparation of Biologically Relevant Conjugates*", Bioconjugate Chem., 1995, 6:150-165.

Zhiyuan Zhang, et al., "*Programmable One-Pot Oligosaccharide Synthesis*", J. Am. Chem. Soc., 1999, 121-734-753.

Ji Zhu, et al., "*Self-Cleaving Ortho Ester Lipids: A New Class of pH-Vulnerable Amphiphiles*", J. Am Chem. Soc., 2000, 122:2645-2646.

Samuel Zalipsky et al., "*New Detachable Poly(ethylene glycol) Conjugates: Cysteine-Cleavable Lipopolymers Regenerating Natural Phospholipid, Diacyl Phosphatidylethanolamine*", Bioconjugate Chemistry, 1999, 10(5):703-707.

* cited by examiner

USE OF OLIGOMERS AND POLYMERS FOR DRUG SOLUBILIZATION, STABILIZATION, AND DELIVERY

CROSS-REFERENCE TO RELATED APPLICATION

This application claims the benefit of U.S. provisional application Ser. No. 60/343,483, filed Dec. 21, 2001, which is incorporated herein by reference.

FIELD OF THE INVENTION

The invention relates to the use of oilgomers and polymers capable of rendering insoluble drugs soluble, protecting unstable drugs, and facilitating the delivery of drugs to their site of action. This invention further relates to processes for the preparation of such oilgomers and polymers, and to compositions containing them.

BACKGOUND OF THE INVENTION

Medicinal and veterinary drugs are only effective if they are able to reach their site of action in the body of the human or animal. There are a number of situations in which drug molecules cannot reach their site of action, preventing many potential drug candidates from being utilized. These situations include those where the drugs (1) are poorly soluble in the relevant physiological fluids, such as blood serum or digestive fluids, (2) are unstable due to the action of enzymes, extremes of pH, or other physiological conditions, (3) are unable to cross various barriers, such as epithelial, mucosal, or membranous barriers, (4) stimulate an undesired immune response, and/or (5) are excreted from the bloodstream via the kidneys.

Some specific drug delivery problems for which there is no general solution include (1) the lack of oral bioavailability of hydrophobic drugs, (2) the inability of injectable drugs intended for treatment of diseases or conditions of the brain or nervous system to reach their site of action due to poor solubility or an inability to cross the blood-brain barrier, (3) the inability of hydrophilic drugs in general to cross mucosal and epithelial barriers, such as the intestinal mucosa, and (4) the inability of hydrophilic drugs to access targets inside of cells because of an inability to cross cellular membranes. In addition, the delivery of hydrophilic drugs such as proteins, peptides, nucleic acids, and other macromolecules is hampered by the degradation of these molecules in intestinal fluids or blood serum as well as renal clearance and immunogenicity.

A number of approaches have resolved some of these issues in specific cases, but there is yet no general solution to the problems of drug delivery. Some examples of existing approaches for solving these problems include (1) solublization of hydrophobic drugs in micelles formed from surfactants in aqueous media (Wiedmann and Kamel, *J. Pharm. Sci.* 2002, 91, 1743; MacGregor, et al., *Adv. Drug Deliv. Rev.* 1997, 25, 33), (2) encapsulation of drugs in polymeric matrices in the nanometer to micrometer size range which may be biodegradable and may contain bioadhesive functional groups or ligands (WO 02/15877, WO 02/49676), (3) encapsulation of hydrophilic drugs in liposomes (Anderson, et al., *Pharm. Res.* 2001, 18, 316; WO 99/33940), which may also display bioadhesive functional groups or ligands, (4) conjugation of drugs to molecules that are substrates for active transport systems (Kramer, et al., *J. Biol. Chem.* 1994, 269, 10621; WO 01/09163; US 2002/0098999), and (5) chemical derivatization of protein drugs with hydrophilic polymers to protect them from degradation, immune recognition, or renal excretion (Belcheva, et al., *Bioconjugate Chem.* 1999, 10, 932; Zalipsky, *Bioconjugate Chem.* 1995, 6, 150; U.S. Pat. No. 4,002,531; U.S. Pat. No. 4,179,337). None of these approaches, however, offers a general solution for all cases of drug delivery problems.

One deficiency of the micellar, liposomal, and polymeric nanoparticulate systems is the inability to tightly control the size of the complexes (particle size). There is substantial evidence that particles of specific size in the nanometer size range (5-100 nm) are especially capable of traversing epithelial, mucosal, and membranous barriers (Florence, et al., *J. Control. Rel.* 2000, 65, 253; Desai, et al., *Pharm. Res.* 1996, 13, 1838; WO 99/65467). A technology able to generate perfectly or nearly monodisperse populations of particles with the ability to control particle size at will has the potential to enhance uptake and tightly control the pharmacokinetics of the drugs being delivered. Technologies for generating liposomes of small size are especially lacking, as are methods to load these vesicles, such that most or all of the drug is contained within the interior aqueous compartment, rather than in the extraliposomal solution.

A second deficiency of current drug delivery strategies is the inability of existing systems to incorporate all of the functions required for delivery into a single system. For example, micelles have been used to solublize hydrophobic drugs, but have no means to target the drug to the intestinal mucosa and enhance permeation of the barrier. Nanoparticulate systems can protect proteins from the low pH and proteolytic enzymes of the stomach, but have not been designed to then protect these proteins in blood serum or lymph. These systems can also contain bioadhesive groups or ligands, but there is no way to regulate the presentation of these moieties to control the timing of adhesive and binding interactions or transmembrane or intracellular transport.

A third deficiency, which applies specifically to the stabilization of proteins by hydrophilic polymers, is that existing methods require covalent attachment of the polymers, such as poly(ethyleneglycol) (PEG) or oligosaccharides, at defined locations that do not interfere with binding. Current technology requires development of expression systems capable of post-translational attachment of oligosaccharides at these sites, random chemical derivatization with PEG, which can decrease activity, or laborious chemical synthesis of proteins to allow synthetic polymers to be attached to desired residues (WO 02/19963, WO 02/20033). In order to avoid attaching hydrophilic polymers at locations that interfere with the biological activity of a protein, detailed knowledge of the 3-dimensional structure of that protein, including its interaction with its binding partners, is required.

SUMMARY OF THE INVENTION

The present invention provides a surfactant comprising a hydrophobic element having a log P value greater than 0 covalently attached to a hydrophilic element, wherein the hydrophobic element has a molecular weight of between about 10-2000 daltons, and wherein the surfactant is capable of forming a micelle that encapsulates a hydrophobic drug. The micelle has a core comprising the hydrophobic drug, wherein the core is substantially free of the hydrophobic element.

The present invention further provides a micelle for encapsulating a hydrophobic drug comprising a plurality of surfactants of the present invention, wherein the micelle has a core comprising the hydrophobic drug, and wherein the core is substantially free of the hydrophobic element.

The present invention further provides a surfactant comprising a first hydrophilic element covalently attached to a first end of a hydrophobic element and a second hydrophilic element covalently attached to a second end of the hydrophobic element, wherein the first and second hydrophilic elements are different in size and/or shape, and wherein the surfactant is capable of forming a micelle that has a core comprising a hydrophilic drug.

The present invention further provides a micelle for encapsulating a hydrophilic drug comprising a plurality of surfactants of the present invention.

The present invention further provides oligomers, polymers, and/or mixtures thereof for the protection of a protein drug comprising at least one recognition element covalently attached to a hydrophilic clement, wherein the recognition element or elements interact noncovalently with the protein drug to form a complex in which the protein drug is protected from degradation, recognition by the immune system, and/or renal excretion.

The present invention further provides a complex comprising at least one oligomer or polymer and a protein drug, wherein the oligomer or polymer comprises at least one recognition element covalently attached to a hydrophilic element, wherein the recognition element or elements interact noncovalently with the protein drug to form a complex in which the protein drug is protected from degradation, recognition by the immune system, and/or renal excretion.

DESCRIPTION OF THE DRAWINGS

It is to be understood that the disclosed drawings are merely exemplary schematic representations of the invention that may be embodied in various forms. The figures are not necessarily drawn to scale, as some features may be exaggerated to show details of particular components. Therefore, specific structural and functional details disclosed herein are not to be interpreted as limiting, but merely as a basis for the claims and as a representative basis for teaching one skilled in the art to variously employ the present invention.

ABBREVIATIONS AND DEFINITIONS

Figure 1:
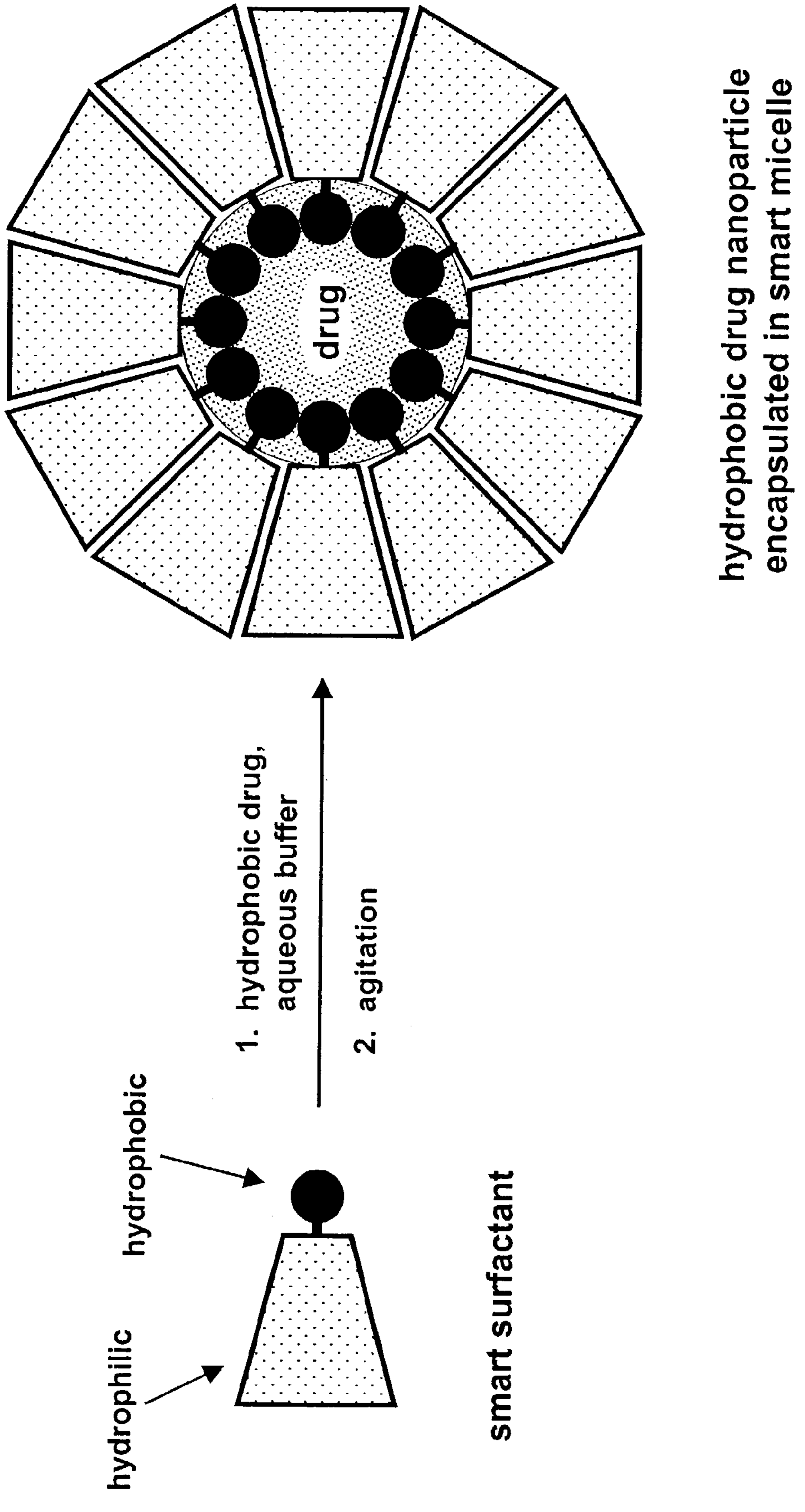
FIG. 1: Schematic drawing showing the self-assembly of a smart micelle comprising a hydrophobic drug for the delivery of that drug. The smart surfactant is depicted as a hydrophilic element covalently attached to a hydrophobic element. Combining the surfactant with a hydrophobic drug in an aqueous buffer and applying mechanical agitation causes the self-assembly of a smart micelle comprising the hydrophobic drug at its core, depicted here in a cross-sectional view. The hydrophobic elements of the surfactant molecules interact with the drug particle, while the hydrophilic elements are oriented to interact with the exterior aqueous environment, as well as with the hydrophilic elements of neighboring surfactant molecules in a lateral fashion.

ADA: adenosine deaminase. BBB: blood brain barrier. BE: binding element. TE: transport element. CNS: central nervous system. DBU: 1,8-diazabicyclo[5.4.0]undec-7-ene. DIEA: N,N-diisopropylethylamine. DMF: N,N-dimethylformamide. EPO: erythropoietin. Fmoc: N-(9-fluorenylmethoxycarbonyl). HBTU: O-benzotriazol-1-yl-N,N,N',N'-tetramethyluronium hexafluorophosphate. HCV: hepatitis C virus. HPLC: high pressure liquid chromatography. NLS: nuclear localization sequence. PBS: phosphate-buffered saline. PEG: poly(ethyleneglycol). PLE: polar loading element. PVP: poly(vinylpyrrolidone). RNA: ribonucleic acid. TFA: trifluoroacetic acid.

The term "drug" means a biologically-active molecule.

The term "hydrophobic," as it refers to the hydrophobic element of surfactants for forming hydrophobic-core micelles that encapsulate hydrophobic drugs, means preferably having a log P value of greater than 0. Log P values measure the partitioning of a molecule between an octanol-rich and a water-rich layer in contact with one another (see CRC Handbook of Chemistry and Physics, $79^{th}$ edition, Lide, ed., pp. 16-42-16-46, CRC Press, 1998; and references within, all of which are incorporated herein by reference). Log P values are measured at a nominal temperature of 25 C. More preferably, hydrophobic means having a log P value greater than about 0.5, even more preferably a log P value greater than about 1, even more preferably a log P value greater than about 1.5, and most preferably a log P value greater than about 2. In this regard, poly(ϵ-caprolactones), such as those disclosed in U.S. Pat. No. 6,322,805, are not within the scope of the hydrophobic element as it pertains to surfactants for forming hydrophobic-core micelles. Using a table of log P values such as that found in the above-mentioned reference to estimate the log P value of poly(ϵ-caprolactone), a value of about 1.8 is obtained, 1.82 being the log P value for butyl acetate, which can be viewed as being similar to the repeat unit of poly(ϵ-caprolactone) in terms of its relative aliphatic content and the presence of the ester functional group. As this is only an estimate based on the perceived similarities between butyl acetate and poly(ϵ-caprolactone), it is contemplated that the actual log P value of poly(ϵ-caprolactone) may vary somewhat from the value of 1.8. Using a similar analysis, poly(lactic acid), also claimed in U.S. Pat. No. 6,322,805 for use as a hydrophobic element, has a log P value of approximately 0.2, using the log P of methyl acetate (log P=0.18) as a gauge.

The phrase "substantially free of the hydrophobic element," as it refers to the core of a micelle encapsulating a hydrophobic drug means preferably less than about 50% hydrophobic element, more preferably less than about 30% hydrophobic element, even more preferably less than about 10% hydrophobic element, even more preferably less than about 5% hydrophobic element, even more preferably less than about 3% hydrophobic element, and most preferably less than about 1% hydrophobic element by weight, in which such comparisons are being made to the total mass of the hydrophobic core, which comprises the hydrophobic drug, the hydrophobic element, and any other hydrophobic molecules or moieties present, such as, but not limited to enzyme inhibitors and permeation enhancers.

The phrase "large volume," as it refers to the drug content of a micelle encapsulating a hydrophobic drug, is a relative term that depends upon the size of the micelle, as well as assumptions about the thickness of the hydrophilic layer of such micelles, and the relative lack of hydrophobic element in the core. It is assumed that a hydrophilic layer as thin as 5 nm will be sufficient to form a stable micelle, given that the shape of the surfactant is sufficiently optimal to allow the hydrophilic elements of adjacent surfactant molecules to interact strongly with each other. Based on this assumption, when calculating the drug volume as a percent of the total volume defined by the outer hydrodynamic diameter of the micelle, a 15 nm diameter micelle will contain at least about 3% drug, a 20 nm diameter micelle will contain at least about 10% drug, a 30 nm diameter micelle will contain at least about 25% drug, a 40 nm diameter micelle will contain at least about 35% drug, a 60 nm diameter micelle will contain at least about 50% drug, an 80 nm diameter micelle will contain at least about 60% drug, and a 100 nm diameter micelle will contain at least about 65% drug. It should be noted that these numbers are not directly comparable to those calculated on a weight basis for a number of reasons. First, as is noted above, the drug loading of a micelle depends upon its size. Second, such percentages may not be based on the total weight or mass of the micelle, but rather the weight or mass of the surfactant alone. Finally, the density of the hydrophobic core may vary considerably depending on how tightly the core is packed, and the density of the hydrophilic layer may also vary depending on how optimal the interactions are among the hydrophilic elements of adjacent surfactants (which will affect the access of the bulk exterior solvent to this layer). The density of the core and the hydrophilic layer may also be significantly different from each other. It is therefore not straightforward to convert percentages based upon volume to those based upon weight or mass.

The term "analog" means a molecule with a structure closely related to that of the parent compound, including homologs, geometric and stereochemical isomers, precursors, derivatives, etc.

The phrase "narrow distribution," as it refers to chain lengths means such a distribution for which the standard deviation about the mean chain length is about ±20%.

The phrase "binding element" refers to a moiety or molecule that is capable of interacting with a receptor or a mucosal, epithelial, or membranous barrier or layer. A binding element can be a simple functional group such as for example a cationic group or a thiol, known as "bioadhesive functional groups," which are known to interact with mucosal layers. A binding element can also be a ligand capable of binding to a protein receptor. Many examples of these are known in the art. All such binding elements known in the art are considered equally useful for the purposes of the current invention. Further, it is contemplated that new binding elements will be conceived, invented, or discovered in the future, and that these new binding elements will be equally useful for the purposes of the current invention.

The phrase "transport element" refers to a moiety or molecule that is capable of carrying an attached cargo into or through a membranous barrier or a portal in a membranous barrier. The membranous barrier can be any membranous barrier, such as a cellular membrane or intracellular membrane. Many examples of these are known in the art, and include membrane-traversing molecules such as peptides or unnatural stepwise oligomers bearing cationic (especially guanidinium) groups, and also include peptidic nuclear localization sequences that are capable of entering a cellular nucleus through nuclear membranes, especially via pores in the nuclear membranes. All such transport elements known in the art are considered equally useful for the purposes of the current invention. Further, it is contemplated that new transport elements will be conceived, invented, or discovered in the future, and that these new transport elements will be equally useful for the purposes of the current invention.

The concepts of size and shape as used in the current invention can be thought of in either geometrical or hydrodynamic terms. The term geometrical in this context refers to those sizes and shapes that are generated by a chemical moiety due to its covalent and 3-dimensional structure, wherein that structure is in an energetically-preferred conformation, but is assumed to be static. The term hydrodynamic in this context refers to those sizes and shapes that are the result of movement of a chemical moiety in solution on a given timescale, such that other molecules or chemical moieties are prevented from occupying the same space on a similar timescale. The term hydrodynamic thus includes the concept of the generation of an excluded volume due to the motions of a chemical moiety. The concept of size can also be thought of in terms of the molecular weight of a molecule or chemical moiety.

The phrase "cone-like" refers to shapes generated by surfactant molecules or portions of surfactant molecules used to generate micelles, in which, as the surfactant is traversed longitudinally from the end closest to the core of the micelle to the end furthest from the core of the micelle, the radial dimensions of the surfactant increase, defined in terms of molecular weight, or in geometrical or hydrodynamic terms.

The phrase "permeation-enhancing molecule" means any molecule capable of increasing the ability of a drug to cross a barrier to delivery. Examples of such barriers include membranous, mucosal, or epithelial barriers. Permeation-enhancing molecules may achieve these results by any mechanism, examples of such mechanisms being increasing the porosity of membrane bilayers, lowering the energy barriers for crossing a membrane, and opening of tight junctions between the cells that form the barrier. Many such permeation-enhancing molecules are known in the art, and some examples include EDTA, sodium lauryl sulfate, sodium caprate, saponins, bile salts, sugar esters such as n-lauryl-β-D-maltopyranoside and sucrose palmitate, polycationic materials, and mannitol. All such permeation-enhancing molecules known in the art are considered equally useful for the purposes of the current invention. Further, it is contemplated that new permeation-enhancing molecules will be conceived, invented, or discovered in the future, and that these new permeation-enhancing molecules will be equally useful for the purposes of the current invention.

The term "undesirable," as it refers to enzymatic activities, means enzymatic activities such as those of P-glycoprotein, cytochrome P450 3A, nucleases, proteases, esterases, and other enzymes, that result in alteration of the chemical or 3-dimensional structure of the drug or that prevent the drug from reaching its site of action, such that the drug does not have or loses its intended biological activity.

The phrase "self-assembly" refers to a process by which molecules are capable of arranging themselves with respect to each other in a particular way to form a complex without additional outside intervention. If additional outside intervention is required in particular cases, it will generally require only an input of energy via mechanical agitation, and potentially dissolution of a molecule in a solvent so as to aid its dispersion in an aqueous medium.

The phrase "unnatural stepwise oligomers" refer to those oligomers that can be synthesized by the addition of a single monomer or submonomer at a time, such that oligomers of a single length and chemical composition may be generated. These oligomers also have a structure that does not occur in nature, hence the term unnatural. Many examples of such unnatural stepwise oligomers are known in the art, and include examples such as peptoids, oligocarbamates, and oligoureas. Many others are known in the art, and are contemplated to be equally as useful as those specifically mentioned for the purposes of the current invention. It is also contemplated that new types of unnatural stepwise oligomers will be conceived of and invented in the future, and that these new unnatural stepwise oligomers will also be equally useful for the purposes of the current invention.

The phrase "traceless linker" refers to a covalent linkage connecting two chemical moieties that can be cleaved under some set of conditions, especially physiological conditions, such that all remnants of the linker are removed from either or both chemical moieties, and that these moieties are released in their free, unmodified form. Many examples of such traceless linkers are known in the art. All such traceless linkers known in the art are considered equally useful for the purposes of the current invention. Further, it is contemplated that new traceless linkers will be conceived, invented, or discovered in the future, and that these new traceless linkers will be equally useful for the purposes of the current invention.

The term "prodrug" refers to the form of a chemical moiety in which a protective chemical group or a linker is attached covalently to that moiety, and which is cleaved under some set of physiological conditions to release the moiety in its free, unmodified form. Many examples of such prodrugs are known in the art. All such prodrugs known in the art are considered equally useful for the purposes of the current invention. Further, it is contemplated that new prodrugs will be conceived, invented, or discovered in the future, and that these new prodrugs will be equally useful for the purposes of the current invention.

The phrase "reactive chemical group" refers to those functional groups or chemical moieties capable of reacting with a functional group in a protein. Many examples of such reactive chemical groups are known in the art for the purposes of conjugating molecules to proteins (Lemieux and Bertozzi, *Trends Biotechnol.* 1998, 16, 506; Hermanson, *Bioconjugate Techniques*, Academic Press, 1996; Means and Feeney, *Chemical Modification of Proteins*, Holden-Day, 1971; Pierce Chemical Company catalog, 2001-2002, pp. 294-362; and references within, all of which are incorporated herein by reference), and include active esters, activated disulfides, maleimides, photoreactive groups, etc. These reactive chemical groups can react with functional groups found in proteins such as amino, hydroxyl, and thiol groups, as well as others. The phrase "reactive linker" refers to covalent linkers containing reactive chemical groups.

The present invention provides basic technologies that can be used to solve general drug delivery problems. For instance, "smart" surfactants can be used to improve the delivery of hydrophobic (non-polar) and hydrophilic (polar) drugs. The term "smart" refers to specific features that give the surfactants novel properties, which will enable them to compensate for the deficiencies of current drug delivery methods.

DETAILED DESCRIPTION OF THE INVENTION

In one embodiment, the present invention provides a smart surfactant wherein the smart feature is a high degree of control over the particle size of micelles formed from the surfactants. This control results from exact specification of the size and shape of the surfactants through the use of stepwise solid- and solution-phase synthetic methods or chemical conjugation techniques to generate surfactants comprised of a single chemical entity or a tightly controlled distribution of chain lengths.

Combinatorial and parallel synthetic methods, combined with high throughput screening can be used to identify surfactants with desirable properties. Such methods are well known to those skilled in the art. For example, in *Fmoc Solid Phase Peptide Synthesis*, Chan and White, ed.s, Oxford University Press, 2000; and Bodanszky and Bodanszky, *The Practice of peptide Synthesis*, Springer-Verlag, 1984; methods for the synthesis of peptides are described. Methods for the synthesis of oligosaccharides by stepwise synthetic approaches, as well as enzymatic methods have been developed recently (Seeberger and Haase, *Chem. Rev.* 2000, 100, 4349; Fukase, in *Glycoscience* Fraser-Reid, et al., ed.s, 2001, 2, 1621-1660; Flitsch, *Curr. Opin. Chem. Biol.* 2000, 4, 619; Zhang, et al., *J. Am. Chem. Soc.* 1999, 121, 734). Stepwise solid-phase chemical syntheses of unnatural oligomers such as peptoids, oligocarbamates, and oligoureas are also known. See Barron and Zuckermann, *Curr. Opin. Chem. Biol.* 1999, 3, 681; Soth and Nowick, *Curr. Opin. Chem. Biol.* 1997, 1, 120; Guichard, in *Solid-Phase Synthesis*, Kates and Albericio, ed.s, Marcel Dekker, 2000, 649-703, all of which are incorporated herein by reference. Combinatorial methods are well known in the art (Bunin, *The Combinatorial Index*, Academic Press, 1998), as are methods for chemical conjugation (Lemieux and Bertozzi, *Trends Biotechnol.* 1998, 16, 506; Hermanson, *Bioconjugate Techniques*, Academic Press, 1996).

In another embodiment, the present invention provides a smart surfactant wherein the smart feature is the inclusion of linkages within the hydrophilic portions of the surfactants which break down under specific conditions, such as a change in pH, the presence of enzymatic activity, or the presence of reducing conditions. In this embodiment, triggering mechanisms can be used to unmask a binding element, a transport element, and/or a linker hidden within the hydrophilic portion of the surfactants, allowing for targeting and adhesion to, or transport through or within, mucosal, epithelial, or membranous barriers to increase permeation (Hussain, *Adv. Drug Deliv. Rev.* 2000, 43, 95; Kast and Bernkop-Schnürch, *Biomaterials* 2001, 22, 2345, both of which are incorporated herein by reference). Alternatively, or in addition, the decomposition of the hydrophilic portion of the surfactant can be designed to destabilize the micellar coating, causing the drug cargo to be released or exposed and thus more available for absorption. The decomposition of the surfactant can also be designed to generate an agent that possesses permeation-enhancing properties that increase the ability of the drug cargo to cross a mucosal, epithelial, or membranous barrier.

The smart surfactants of the present invention are "self-emulsifying," which involves a process of mixing the drug and surfactant in an aqueous buffer, and applying gentle mechanical agitation to form the micelles by a self-assembly process (Craig, et al., *Drugs Pharm. Sci.* 2000, 105, 323). Alternatively, an insoluble hydrophobic drug can first be dissolved in a volatile solvent system or FDA-approved oils before dispersion in the smart-surfactant-laden aqueous phase. The smart surfactants and their physiological breakdown products will also comprise chemical entities that are non-toxic, non-immunogenic, and readily excretable.

In a particular embodiment, the present invention provides smart surfactants, which encapsulate and deliver hydrophilic drugs, that also contain a "polar loading element" (PLE), which enables these surfactants to incorporate all or nearly all of the hydrophilic drug into the core of the micelle, with little or none remaining in the extramicellar aqueous solution.

Additional specific features of the smart surfactants are described in detail below.

In another embodiment, the present invention provides a method of protecting protein drugs from degradation, renal excretion, and immune recognition using oligomers, polymers, and mixtures thereof, but without requiring chemical modification of the protein, and without interfering with the biological activity of the protein. This embodiment relies upon the discovery of ligands that bind noncovalently to the protein but not to the active site of the protein. Methods are provided for the discovery of these ligands and their use in protecting a protein via conjugation to oligomers, polymers, and mixtures thereof. The lack of covalent modification of the protein simplifies the synthesis and formulation processes used to generate the protected protein. Both the protein and oligomers, polymers, and mixtures thereof can be rigorously purified prior to the formulation process, and no subsequent purification is required once the complex has been formed.

Smart Surfactants for the Encapsulation and Delivery of Hydrophobic Drugs

The basic structure of the smart surfactants for the encapsulation and delivery of hydrophobic drugs is shown schematically in FIG. 1. A hydrophobic element is covalently attached to a hydrophilic element. The covalent attachment is noncleavable or cleavable under physiological conditions. The hydrophobic element interacts with the hydrophobic drug, without significantly interpenetrating the hydrophobic drug particle at the core of the micelle, such that the hydrophobic drug nanoparticle is predominantly pure drug and substantially free of the hydrophobic element. This is a novel feature of the micelles formed with these surfactants, and differs from those formed from amphiphilic diblock or triblock copolymers in the prior art, in which the hydrophobic core is traversed and/or deeply penetrated by hydrophobic polymer chains, thereby greatly reducing the amount of drug that can be loaded into the core (Yamamoto, et al., *J. Control. Rel.* 2001, 77, 27; Lavasanifar, et al., *Adv. Drug Deliv. Rev.* 2002, 54, 169; Kwon, et al., *J. Control. Rel.* 1994, 29, 17; U.S. Pat. No. 6,322,805). The smart surfactant and its physiological breakdown products are non-toxic, non-immunogenic, and readily excretable.

The desired effect of a hydrophobic drug core of substantially pure drug, and therefore a high loading capacity, is achieved in the current invention by use of a small hydrophobic element, rather than a long polymer chain. In the current invention, the hydrophobic element is a small molecule, an oligomer, or a polymer. Preferably, the oligomer or polymer has a single chain length or a narrow distribution of chain lengths. Suitable oligomers or polymers include peptides having hydrophobic side chains and unnatural stepwise oligomers having hydrophobic side chains such as peptoids, oligocarbamates, oligoureas, and mixtures thereof. When the oligomer or polymer is a peptide, it is preferably a short peptide comprising less than about 20 amino acids, more preferably between about 2-20 amino acids, more preferably between about 2-15 amino acids, more preferably between about 2-10 amino acids, and most preferably between about 2-5 amino acids. Suitable small molecules include the hydrophobic drug itself or an analog thereof, cholesterol, cholesterol derivatives, bile acids, bile acid derivatives, steroidal sapogenins, triterpenoid sapogenins, steroidal sapogenin derivatives, triterpenoid sapogenin derivatives, steroid derivatives, amino acids including aromatic amino acids, and mixtures thereof.

The hydrophilic element is intended to orient itself toward the bulk aqueous solution upon formation of the micelle, and additionally may interact in a lateral fashion with the hydrophilic elements of different, but adjacent surfactant molecules (e.g. via hydrogen bonding or charge/charge interactions). This lateral interaction may be strong enough to stabilize the micellar structure. This additional stabilization allows the use of a relatively small hydrophobic element, as discussed above, with only a modest affinity for the hydrophobic drug core.

The hydrophilic element is an oligomer or polymer. Preferably the oligomer or polymer has a single chain length or a narrow distribution of chain lengths. Also preferably the oligomer or polymer has a linear, branched, or cyclic structure, and/or includes side chains of gradually increasing size to generate a cone-like shape. Suitable oligomers or polymers include oligosaccharides, polysaccharides, peptides, unnatural stepwise oligomers, and mixtures thereof. More specifically, suitable oligomers or polymers may include poly(ethyleneglycol) (PEG), poly(propyleneglycol), poly(vinylpyrrolidone) (PVP), poly(hydroxyethylmethacrylate), poly($\epsilon$-caprolactone), poly(lactic acid), poly(glycolic acid), peptoids, oligocarbamates, oligoureas, and mixtures thereof. The peptides and unnatural stepwise oligomers may bear hydrophilic side chains such as PEG oligomers, PVP oligomers, monosaccharides, oligosaccharides, and cyclodextrins or those side chains comprising polar functional groups such as —OR (wherein R is hydrogen or an alkyl or aromatic group), —CONRR' (wherein R and R' are independently hydrogen or an alkyl or aromatic group), —NRR' (wherein R and R' are independently hydrogen or an alkyl or aromatic group), —NR(CNR'(NR"R''')) (wherein R, R', R", and R''' are independently hydrogen or an alkyl or aromatic group), —COOR (wherein R is a hydrogen or an alkyl or aromatic group), —$SO_3$R (wherein R is a hydrogen or an alkyl or aromatic group), —P(O)(OR)(OR') (wherein R and R' are independently hydrogen or an alkyl or aromatic group), —NRR'R"(+) (wherein R, R', and R" are all alkyl or aromatic groups), and mixtures thereof.

The hydrophilic element may further comprise labile linkages that are capable of being cleaved under specific physiological conditions including, for example, pH, presence of enzymatic activity, oxidizing or reducing conditions, presence of nucleophiles, etc. Suitable linkers comprise functional groups such as amides, carbamates, thiocarbamates, oxygen esters, thioesters, glycolate esters, lactate esters, orthoesters, acetals, ketals, phosphodiesters, disulfides, and mixtures thereof. The linker as depicted in FIG. 1 can be any covalent linkage, and can be stable or cleavable under physiological conditions. In a particular embodiment, the linkers are capable of generating a permeation-enhancing molecule as further described below. In another particular embodiment, the linkers are capable of unmasking an element selected from the group consisting of binding elements and transport elements as further described below.

The hydrophilic element itself may further comprise binding elements and/or transport elements. Suitable binding elements include elements selected from the group consisting of ligands, bioadhesive functional groups, and mixtures thereof. Suitable transport elements include elements selected from the group consisting of nuclear localization sequences, membrane-traversing molecules, and mixtures thereof.

The hydrophobic element of the surfactant interacts preferentially with the hydrophobic drug particle. The micelle thus formed has a hydrodynamic diameter in the range of from about 1-100 nm, and preferably about 5-80 nm. The hydrophilic element is oriented to interact with the external aqueous environment, but may also interact significantly in a lateral fashion with the hydrophilic elements of adjacent surfactant molecules, such that the micellar structure is stabilized.

The smart surfactant will be used to form a micelle containing the hydrophobic drug at its core via a self-assembly process, shown schematically in FIG. 1. The micelle therefore comprises a plurality of surfactants for encapsulating a hydrophobic drug, wherein the micelle has a core comprising the hydrophobic drug, wherein the core is substantially free of the hydrophobic element. In a preferred embodiment, the micelle comprises a large volume of the hydrophobic drug. As mentioned above, the micelles can be formed by a self-assembly process, which comprises the steps of combining a smart surfactant with a hydrophobic drug in an aqueous buffer and gently agitating to form micelles in which the hydrophobic drug is sequestered at the core of the micelle. The system is thus of the self-emulsifying type. Alternatively, micelles are formed by a method comprising dissolving the hydrophobic drug in a volatile solvent or FDA-approved oil to facilitate the dissolution of the drug and adding the dissolved drug to an aqueous solution comprising the surfactant.

Figure 2:
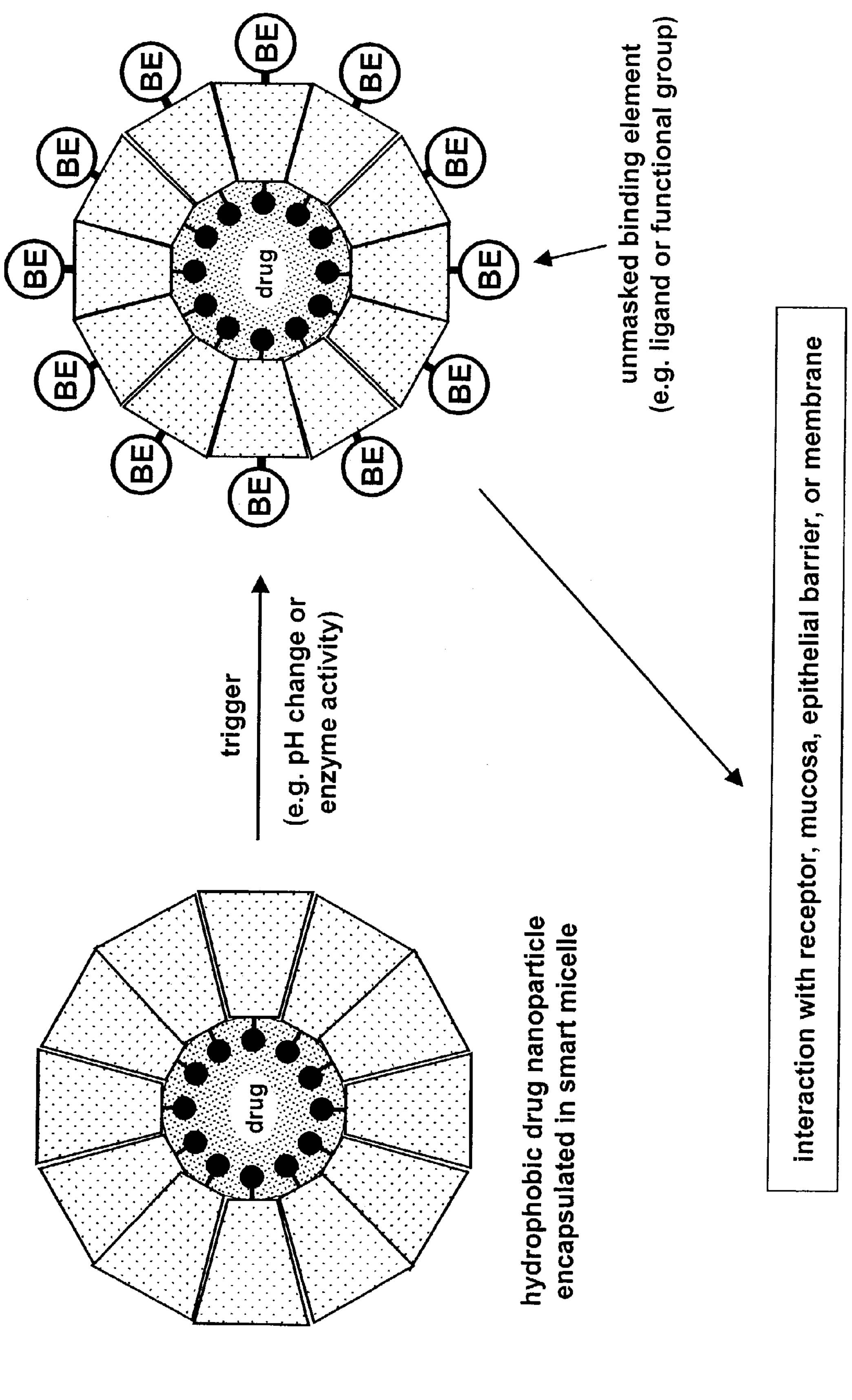
FIG. 2: Schematic drawing depicting the unmasking of a binding element (BE) in a smart micelle. A smart micelle encapsulating a hydrophobic drug particle is exposed to conditions (such as a change in pH or exposure to enzymatic activity), which triggers controlled decomposition to reveal a binding element (BE) capable of binding to or interacting with a barrier to delivery. Once unmasked, the binding element causes the micelle to interact with, adhere to, or bind to a receptor, mucosal layer, epithelial barrier, or membrane, resulting in enhanced uptake across that barrier.
Figure 3:
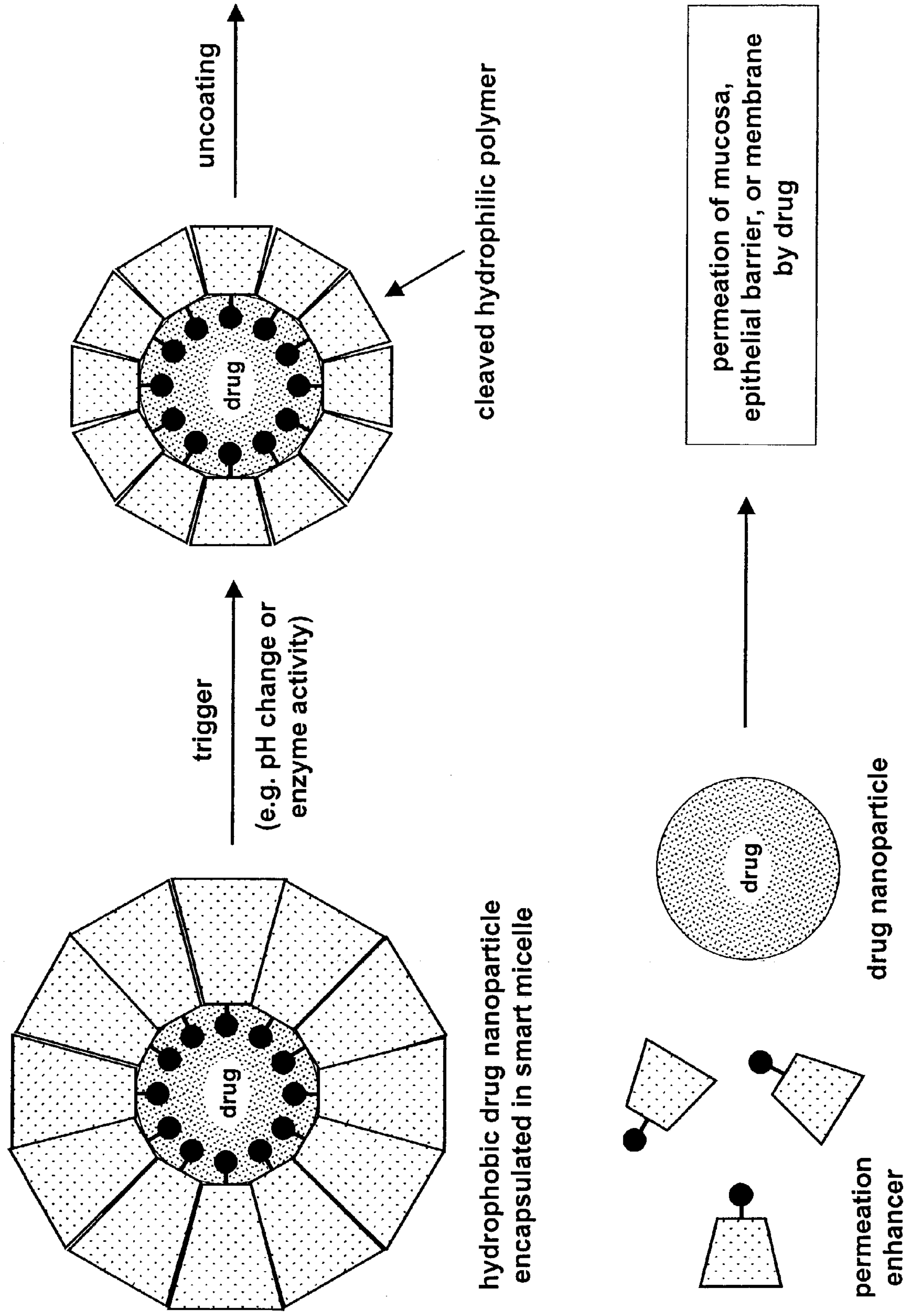
FIG. 3: Schematic drawing depicting the uncoating of a drug particle and the enhancement of its uptake across a barrier to delivery. Depicted is a hydrophobic drug particle encapsulated in a smart micelle. In response to a trigger (such as a change in pH or exposure to enzymatic activity), the outer hydrophilic element undergoes a controlled decomposition. The associated loss of lateral interactions among the hydrophilic elements causes the coating to become unstable, which results in the exposure of the hydrophobic drug particle and release of the smart surfactant as individual molecules. As depicted here, this process also results in the simultaneous conversion of the smart surfactant into a form in which it is capable of enhancing the permeation of the drug across a barrier to delivery, such as a mucosal surface, epithelial barrier, or a membrane.

The functions of particular smart features of these surfactants and corresponding micelles are depicted in FIGS. 2 and 3. FIG. 2 shows the unmasking of a binding element, which includes, for example, ligands, bioadhesive functional groups, and mixtures thereof. The binding element is initially masked by its incorporation into the chemical structure of the hydrophilic element as a monomer, a linking group, or a chemically-protected functional group. In addition to the binding element, a transport element such as nuclear localization sequences, membrane-traversing molecules, and mixtures thereof, can be incorporated into the chemical structure of the hydrophilic element as a monomer, a linking group, or a chemically-protected functional group. Cleavage of a chemical linkage or group within the hydrophilic element (or the linkage between the hydrophilic and hydrophobic elements) in response to a triggering condition (such as a change in pH, the presence of enzymatic activity, or a change in the reduction potential of the environment) unmasks the binding element or transport element, allowing it to interact with a receptor or a mucosal, epithelial, or membranous barrier. Such an interaction increases the ability of the micelle, or the hydrophobic drug contained within, to permeate the barrier, by, for example, increasing the residence time on the barrier surface, inducing a receptor-mediated transcytosis or endocytosis processes, or penetrating a cellular or nuclear membrane. The binding element or transport element may alternatively not be initially masked, such that no triggering event is required to unmask it.

FIG. 3 depicts the uncoating process of a smart micelle, and subsequent permeation of a mucosal, epithelial, or membranous barrier by the drug. Depicted in cross-sectional view is a smart micelle containing a hydrophobic drug particle. In response to a triggering condition (such as a change in pH, the presence of enzymatic activity, or a change in the reduction potential of the environment), the hydrophilic element partially or completely degrades in a controlled fashion due to the cleavage of an incorporated labile linkage. The size of the hydrophilic element is decreased, as are the stabilizing interactions occurring laterally among the hydrophilic elements of adjacent surfactant molecules. As the stability of the micellar coating decreases, the surfactant molecules disassociate themselves from the hydrophobic drug particle and each other partially or completely, enabling the drug particle to permeate a mucosal, epithelial, or membranous barrier. Thus, the linkers are capable of destabilizing the micelle, whereby a plurality of the surfactants are shed from the core and the hydrophobic drug is exposed to an external environment.

The surfactant molecule of a smart micelle in which the hydrophilic element is partially or completely degraded in this process may also possess the property of enhancing the permeation of the drug into or through the barrier. In one particular embodiment, the hydrophilic element further comprises linkers that are capable of generating a permeation-enhancing molecule. In another particular embodiment, the surfactant itself is a permeation-enhancing molecule. Examples of molecules that enhance permeation are EDTA, sodium lauryl sulfate, sodium caprate, saponins, bile salts, and sugar esters such as n-lauryl-β-D-maltopyranoside and sucrose palmitate (Uchiyama, et al., *J. Pharm. Pharmacol.* 1999, 51, 1241; Fricker, et al., Brit. *J. Pharmacol.* 1996, 117, 217; Nakada, et al., *J. Pharmacobio-Dyn.* 1988, 11, 395; U.S. Pat. No. 5,650,398, all of which are incorporated herein by reference). Hydrophilic polymeric materials bearing multiple positively-charged functional groups are known to increase the permeability of epithelial and mucosal barriers by the paracellular route (Dodane, et al., *Int. J. Pharm.* 1999, 182, 21; Kotzé, et al., *Pharm. Res.* 1997, 14, 1197, both of which are incorporated herein by reference). Mannitol is known to increase the permeability of the blood brain barrier (Koenig, et al., *J. Neurochem.* 1989, 52, 1135; Koenig, et al., *Brain Res.* 1989, 483, 110, both of which are incorporated herein by reference). Oligomeric transporters containing positively charged functional groups, especially guanidinium groups, are known to traverse cellular membranes, carrying an attached cargo into the cellular cytoplasm, into the nucleus, or across epithelial layers (Futaki, et al., *J. Biol. Chem.* 2001, 276, 5836; U.S. Pat. No. 5,807,746; U.S. Pat. No. 5,804,604; Mitchell, et al., *J. Peptide Res.* 2000, 56, 318; Wender, et al., *Proc. Natl. Acad. Sci. USA* 2000, 97, 13003; Wender, et al., *J. Am. Chem. Soc.* 2002, 124, 13382; WO 01/62297; WO 02/069930, all of which are incorporated herein by reference).

The uncoating and permeation process shown in FIG. 3 can also occur contemporaneously with the unmasking of a binding element or a transport element (and its subsequent interaction with its target). The micelle can further comprise inhibitors of undesirable enzymatic activities, such as those of P-glycoprotein, cytochrome P450 3A, and proteases, esterases, or nucleases. Additionally, the micelles may further comprise a permeation-enhancing molecule, different from the surfactant.

Smart Surfactants for the Encapsulation and Delivery of Hydrophilic Drugs

Figure 4:
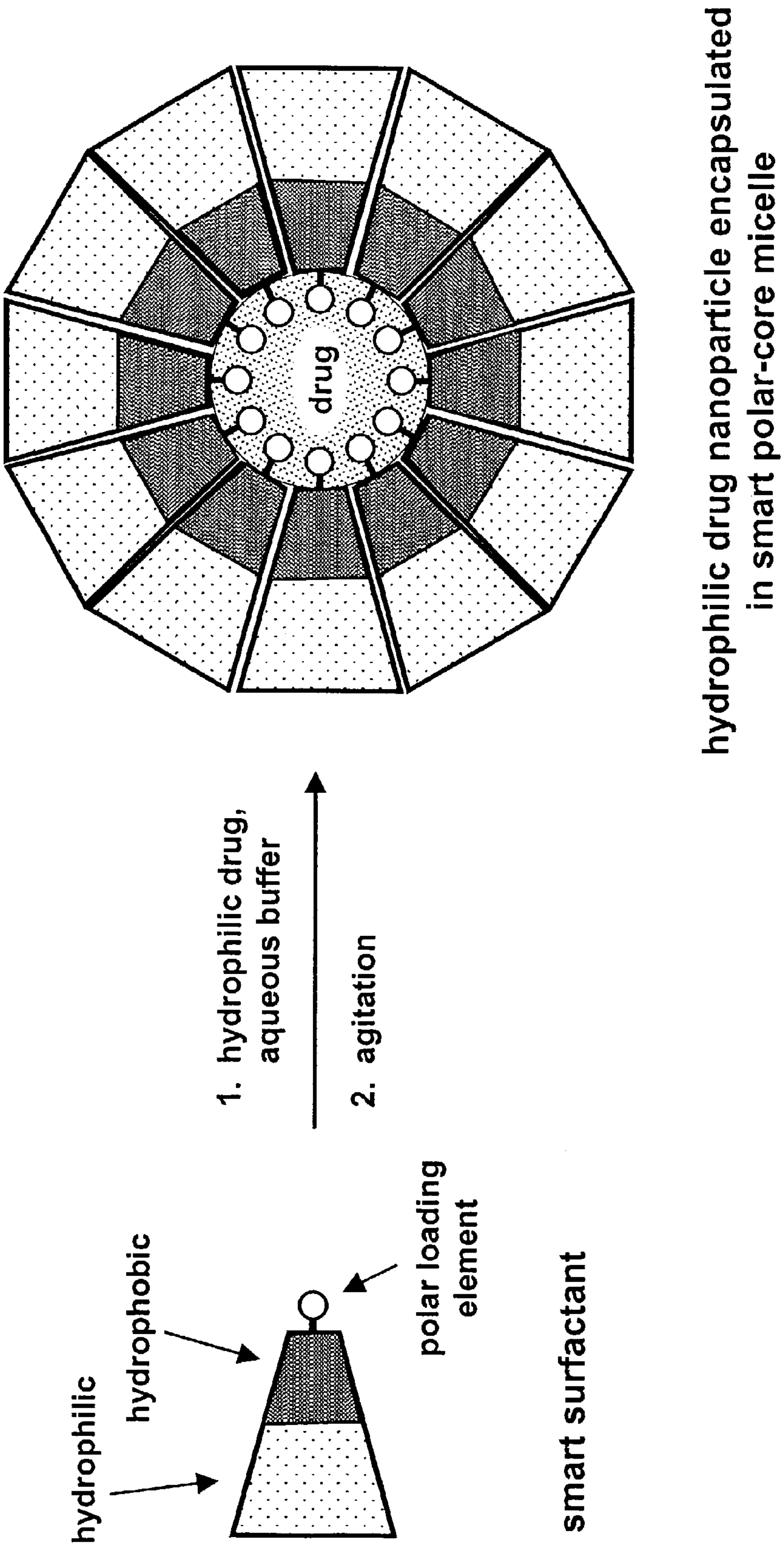
FIG. 4: Schematic drawing showing the self-assembly of a polar-core smart micelle comprising a hydrophilic drug for the delivery of that drug. The smart surfactant is depicted as a hydrophilic element covalently attached to a hydrophobic element, which is covalently linked to a polar loading element (PLE). Combining the surfactant with a hydrophilic drug in an aqueous buffer and applying mechanical agitation causes the self-assembly of a polar-core smart micelle comprising the hydrophilic drug at its core, depicted here in a cross-sectional view. All or a substantial portion of the hydrophilic drug is encapsulated in the micelle, and little or none remains in the aqueous solution outside of the micelle due to the preferential interaction of the drug with the polar loading element. The hydrophobic elements of the surfactant molecules interact with each other in a lateral fashion, stabilizing the complex, as well as effectively sealing the polar core from the external aqueous environment. The particle is also stabilized by the lateral interactions among the hydrophilic elements of adjacent surfactant molecules. These hydrophilic elements are oriented such that they also interact with the exterior aqueous environment.

The basic structure of the smart surfactant for the delivery of hydrophilic drugs is depicted schematically in FIG. 4. A second hydrophilic element is covalently attached to a hydrophobic element, which is covalently attached to a first hydrophilic element termed the "polar loading element" (PLE), wherein the first and second hydrophilic elements are different in size and/or shape, and wherein the surfactant is capable of forming a micelle that has a core comprising a hydrophilic drug. The covalent attachments are noncleavable or cleavable under physiological conditions. The smart surfactant and its physiological breakdown products, are non-toxic, non-immunogenic, and readily excretable.

The desired effect of the PLE is that it is capable of interacting with a hydrophilic drug such that the hydrophilic drug is sequestered in the core. In general, the PLE comprises a chemical structure or functional group that is capable of interacting favorably with the hydrophilic drug, such as a positive or negative charge, a hydrogen-bonding functionality, a ligand that binds noncovalently to the drug, a traceless linker, or a prodrug. In a preferred embodiment, the PLE further comprises a functional group or ligand that is capable of noncovalently binding to the hydrophilic drug. In another preferred embodiment, the PLE further comprises a traceless linker or a prodrug that is capable of being cleaved under physiological conditions, wherein the traceless linker or the prodrug is capable of covalently linking the PLE to the hydrophilic drug. For examples of suitable traceless linkers and prodrugs see Gharat, et al., *Int. J. Pharm.* 2001, 219, 1; Zalipsky, et al., *Bioconjugate Chem.* 1999, 10, 703; Matsumoto, et al., *Bioorg. Med. Chem. Lett.* 2001, 11, 605; Zhu, et al., *J. Am. Chem. Soc.* 2000, 122, 2645; Norbeck, et al., *J. Med. Chem.* 1989, 32, 625; Senter, et al., *J. Org. Chem.* 1990, 55, 2975; WO 01/47562, all of which are incorporated herein by reference.

The hydrophobic element in the micellar structure plays the role of stabilizing the structure by interacting noncovalently with the hydrophobic elements of adjacent surfactant molecules. These interactions also serve to effectively seal the core of the micelle, protecting the drug from conditions in the external medium. In the current embodiment, the hydrophobic element is a small molecule, an oligomer, or a polymer. Preferably, the oligomer or polymer has a single chain length or a narrow distribution of chain lengths. Suitable oligomers or polymers include peptides having hydrophobic side chains and unnatural stepwise oligomers having hydrophobic side chains such as peptoids, oligocarbamates, oligoureas, and mixtures thereof. Suitable small molecules include cholesterol, cholesterol derivatives, bile acids, bile acid derivatives, steroidal sapogenins, triterpenoid sapogenins, steroidal sapogenin derivatives, triterpenoid sapogenin derivatives, steroid derivatives, amino acids, and mixtures thereof.

The second hydrophilic element in the surfactants used to form polar-core micelles may have the same compositions, functions, and smart features as the hydrophilic element described above for the surfactants used to form smart micelles for the encapsulation and delivery of hydrophobic drugs. As such, the second hydrophilic element is an oligomer or polymer. Preferably the oligomer or polymer has a single chain length or a narrow distribution of chain lengths. Also preferably the oligomer or polymer has a linear, branched, or cyclic structure, and/or includes side chains of gradually increasing size to generate a cone-like shape. Suitable oligomers or polymers include oligosaccharides, polysaccharides, peptides, unnatural stepwise oligomers, and mixtures thereof. More specifically, suitable oligomers or polymers may include poly(ethyleneglycol) (PEG), poly(propyleneglycol), poly(vinylpyrrolidone) (PVP), poly(hydroxyethylmethacrylate), poly($\epsilon$-caprolactone), poly(lactic acid), poly(glycolic acid), peptoids, oligocarbamates, oligoureas, and mixtures thereof. The peptides and unnatural stepwise oligomers may bear hydrophilic side chains such as PEG oligomers, PVP oligomers, monosaccharides, oligosaccharides, and cyclodextrins or those side chains comprising polar functional groups such as —OR (wherein R is hydrogen or an alkyl or aromatic group), —CONRR' (wherein R and R' are independently hydrogen or an alkyl or aromatic group), —NRR' (wherein R and R' are independently hydrogen or an alkyl or aromatic group), —NR(CNR'(NR"R''')) (wherein R, R', R", and R''' are independently hydrogen or an alkyl or aromatic group), —COOR (wherein R is a hydrogen or an alkyl or aromatic group), —$SO_3R$ (wherein R is a hydrogen or an alkyl or aromatic group), —P(O)(OR)(OR') (wherein R and R' are independently hydrogen or an alkyl or aromatic group), —NRR'R"(+) (wherein R, R', and R" are all alkyl or aromatic groups), and mixtures thereof.

The second hydrophilic element may further comprise binding elements and/or transport elements. Suitable binding elements include elements selected from the group consisting of ligands, bioadhesive functional groups, and mixtures thereof. Suitable transport elements include elements selected from the group consisting of nuclear localization sequences, membrane-traversing molecules, and mixtures thereof.

The second hydrophilic element may further comprise labile linkages that are capable of being cleaved under specific physiological conditions including, for example, pH, presence of enzymatic activity, oxidizing or reducing conditions, presence of nucleophiles, etc. Suitable linkers comprise functional groups such as include amides, carbamates, thiocarbamates, oxygen esters, thioesters, glycolate esters, lactate esters, orthoesters, acetals, ketals, phosphodiesters, disulfides, and mixtures thereof. In a particular embodiment, the linkers are capable of unmasking an element selected from the group consisting of binding elements and transport elements, as described above. The linker can be any covalent linkage, and can be stable or cleavable under physiological conditions. In another particular embodiment, linkers are capable of destabilizing the micelle, whereby a plurality of the surfactants are shed from the core and the hydrophilic drug is exposed to an external environment. In another particular embodiment, the linkers are capable of generating a permeation-enhancing molecule, as described above. The surfactant itself can also be a permeation-enhancing molecule.

Surfactants of this type form what are termed here as "polar-core micelles," via a self-assembly process, as shown in FIG. 4. The polar-core micelle therefore comprises a plurality of surfactants for encapsulating a hydrophilic drug. The micelle thus formed has a hydrodynamic diameter in the range of from about 1-100 nm, and preferably about 5-80 nm. The micelles are formed by a self-assembly process, which comprises the steps of combining a smart surfactant with a hydrophilic drug in an aqueous buffer and gently agitating to form polar-core micelles (shown in cross section), with the hydrophilic drug encapsulated at its core. The system is therefore of the self-emulsifying type. In a particular embodiment, the core is surrounded by a hydrophobic layer, and the hydrophobic layer is in turn surrounded by a hydrophilic layer.

To ensure consistent formation of micelles in which the PLE is always present at the interior surface, the structure of the smart surfactant is asymmetrical by design. The second hydrophilic block is larger than the PLE, such that the resulting cone-like shape of the smart surfactant ensures self-assembly into the desired structure. In the micelle, the function of the PLE is to preferentially interact with the hydrophilic drug such that the hydrophilic drug is sequestered at the core, with little or none in the surrounding external aqueous medium.

It is anticipated, in the current embodiment, that the differing size and shape of the second hydrophilic element and the PLE will be sufficient to cause the surfactant molecules to orient themselves in a parallel, rather than antiparallel, fashion. However, if additional features are necessary to cause the surfactant chains to orient themselves relative to each other in a parallel fashion, an off-center uncharged polar group can optionally be interposed within the hydrophobic element. The presence of such a polar group within the hydrophobic element will prevent surfactant molecules from aligning antiparallel to each other, since the polar group would then interact with a hydrophobic region of the adjacent surfactant molecule, which is unfavorable energetically. If the surfactant molecules are aligned in a parallel orientation, the uncharged polar groups can interact with each other, which is favorable energetically. This situation occurs in the structure of the naturally-occurring protein GCN4 due to the presence of an asparagine residue, causing the formation of a parallel coiled coil (Gonzalez, et al., *Nature Struct. Biol.* 1996, 3, 1011). Positively and negatively charged groups may also be interposed within the hydrophilic-, hydrophobic-, or polar-loading elements to aid in the self-assembly process, either by favoring the desired micellar structure, or disfavoring an alternative, but undesired structure. This concept can include formation of micelles from an equimolar mixture of two different smart surfactants, each bearing charges of opposite sign.

The structure of the smart surfactants for the formation of polar-core micelle is conceptually a fusion of two surfactant molecules of a liposome, in which the hydrophobic moiety of a surfactant molecule in the outer leaflet of the membrane bilayer is covalently linked to the hydrophobic moiety of a surfactant molecule in the inner leaflet of the bilayer, to form a single molecule of the smart surfactant. The single hydrophobic element of these smart surfactants thus corresponds to the hydrophobic interior of a liposomal membrane bilayer, while the covalently-linked PLE corresponds to the hydrophilic moiety of the inner leaflet surfactant molecule of the liposome, and the second hydrophilic element linked covalently at the other end of the hydrophobic element corresponds to the hydrophilic moiety of the outer leaflet surfactant molecule of the liposome. Fusion of the hydrophobic moieties of two surfactant molecules of a liposomal bilayer in this fashion creates the possibility for much more robust control of the particle size and stability of the resulting polar-core micelles than is possible for conventional liposomes. Such micelles will also be much less likely to leak the entrapped drug than conventional liposomes.

Polar-core micelles are useful for the encapsulation and delivery of a range of hydrophilic molecules, due not only to their hydrophilic interior, but also to the protection afforded by the hydrophobic seal created by lateral interactions among the hydrophobic elements of adjacent surfactant molecules in the micelle. This seal prevents exposure of the encapsulated drug to degradative conditions or enzymatic activities in the outside environment. This feature is especially useful for labile molecules such as peptides, proteins, oligosaccharides, polysaccharides, and nucleic acids.

Specifically, with regard to the delivery of nucleic acids, polar-core micelles may be far superior to current delivery strategies that rely upon condensation of the nucleic acid with a polycationic material, which tightly sequesters the nucleic acid, preventing its facile release at the site of action (Zabner, *Adv. Drug Deliv. Rev.* 1997, 27, 17; U.S. Pat. No. 5,942,634; Byk, et al., *J. Med. Chem.* 1998, 41, 224). Polar-core micelles of the current invention, by contrast, do not rely upon such condensation, and should thus be able to release the nucleic acid more easily and efficiently at the site of action.

Polar-core micelles formed from these surfactants can also comprise inhibitors of undesirable enzymatic activities, such as those of P-glycoprotein, cytochrome P450 3A, and proteases, esterases, or nucleases. Further, the micelles may also comprise a permeation enhancing molecule, different from the surfactant.

Figure 5:
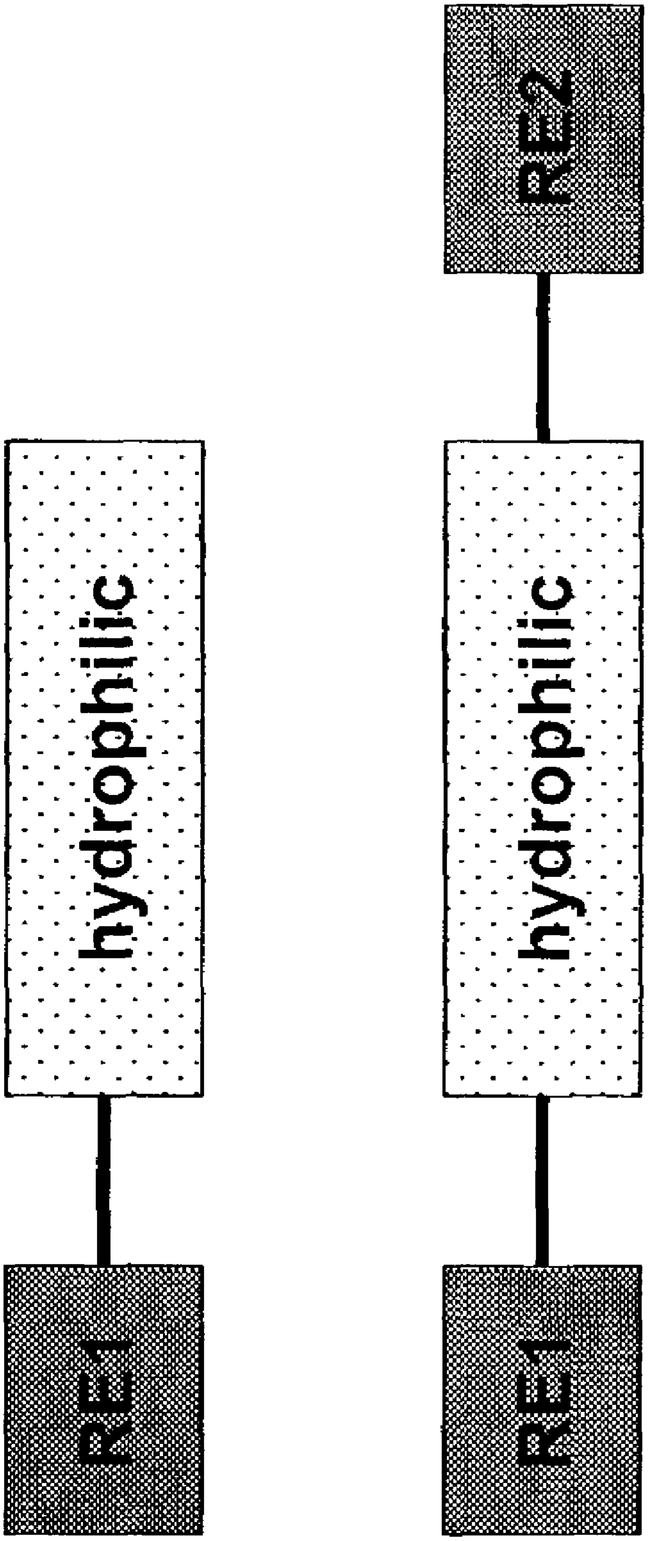
FIG. 5: Schematic representation of a hydrophilic copolymer for the stabilization of a protein drug. The upper drawing depicts a recognition element capable of binding noncovalently to the protein (RE1) linked covalently to a hydrophilic element. The lower drawing shows a hydrophilic element linked covalently at each end to different recognition elements (RE1 and RE2) each capable of binding noncovalently to a different site on the protein.

Oligomers, Polymers, and/or Mixtures thereof for the Protection of Protein Drugs Shown in FIG. 5 is the basic structure of the hydrophilic copolymer for protein drug protection. The upper drawing depicts one version, in which a recognition element (RE1) capable of binding noncovalently to a protein at a site other than its active site is covalently linked to a hydrophilic element. The lower drawing depicts a second version, in which a recognition element (RE1) is linked covalently to a hydrophilic element, which is linked covalently at its other end to a second recognition element (RE2), which is capable of binding noncovalently to the same protein at a site distinct from the binding site of RE1, which is also not the active site of the protein.

In one embodiment, the present invention provides an oligomer, polymer, and/or mixtures thereof for the protection of a protein drug comprising at least one recognition element covalently attached to a hydrophilic element, wherein the recognition element or elements interact noncovalently with the protein drug to form a complex in which the protein drug is protected from degradation, recognition by the immune system, and/or renal excretion. The covalent attachment is noncleavable or cleavable under physiological conditions. The oligomer, polymer, and/or mixtures thereof and its physiological breakdown products, are non-toxic, non-immunogenic, and readily excretable. In a particular embodiment, when the protein drug has an active site, the active site is not obstructed by the oligomer or polymer, thereby maintaining biological activity of the protein drug in the complex.

In another embodiment, the oligomers, polymers, and/or mixtures thereof have a plurality of recognition elements, wherein each recognition element binds to a mutually distinct site on the protein drug, which may be produced by using branched architecture offering multiple chain ends. Alternatively, a plurality of recognition elements may be distributed throughout linear or branched hydrophilic elements at discrete locations. In a particular embodiment, when the PLE of the smart surfactants for the delivery of hydrophilic drugs depicted in FIG. 4 is equivalent to a recognition element (e.g. RE1 or RE2) as described above, that surfactant can then be utilized for the formation of polar-core micelle for the protection and delivery of protein drugs.

The recognition element or element comprise peptides and cyclic peptides (derived from phage library selection as described below), unnatural stepwise oligomers, cyclic unnatural stepwise oligomers, natural small molecules, and synthetic small molecules. Alternatively, the recognition element or element may be peptide or non-peptide ligands discovered by combinatorial chemical methods in which the potential ligand libraries are displayed on a surface or resin beads for assay screening (Burbaum and Sigal, *Curr. Opin. Chem. Biol.* 1997, 1, 72) or selection, and may further be displayed in an arrayed fashion to aid this process. Examples of such molecules include libraries of unnatural stepwise oligomers such as peptoids, oligocarbamates, and oligoureas, or synthetic small molecules such as heterocyclic compounds. The recognition element or elements may further comprise multivalent ligands to increase their affinity for their binding sites.

The hydrophilic element comprises an oligomer or polymer. Preferably the oligomer or polymer has a single chain length or a narrow distribution of chain lengths. Also preferably the hydrophilic element has a branched, linear, or cyclic structure. Suitable oligomers or polymers include oligosaccharides, polysaccharides, peptides, unnatural stepwise oligomers, and mixtures thereof. More specifically, suitable oligomers or polymers may include poly(ethyleneglycol) (PEG), poly(propyleneglycol), poly(vinylpyrrolidone) (PVP), poly(hydroxyethylmethacrylate), poly(ε-caprolactone), poly(lactic acid), poly(glycolic acid), peptoids, oligocarbamates, oligoureas, and mixtures thereof. The peptides and unnatural stepwise oligomers may bear hydrophilic side chains such as PEG oligomers, PVP oligomers, monosaccharides, oligosaccharides, and cyclodextrins or those side chains comprising polar functional groups such as —OR (wherein R is hydrogen or an alkyl or aromatic group), —CONRR' (wherein R and R' are independently hydrogen or an alkyl or aromatic group), —NRR' (wherein R and R' are independently hydrogen or an alkyl or aromatic group), —NR(CNR'(NR"R"')) (wherein R, R', R", and R"' are independently hydrogen or an alkyl or aromatic group), —COOR (wherein R is a hydrogen or an alkyl or aromatic group), —$SO_3R$ (wherein R is a hydrogen or an alkyl or aromatic group), —P(O)(OR)(OR') (wherein R and R' are independently hydrogen or an alkyl or aromatic group), —NRR'R" (+) (wherein R, R', and R" are all alkyl or aromatic groups), and mixtures thereof.

The hydrophilic element may further comprise binding elements and/or transport elements. Suitable binding elements include elements selected from the group consisting of ligands, bioadhesive functional groups, and mixtures thereof. Suitable transport elements include elements selected from the group consisting of nuclear localization sequences, membrane-traversing molecules, and mixtures thereof. The hydrophilic element may further comprise positively or negatively charged groups covalently linked to or within its structure in masked or unmasked form.

The hydrophilic element may further comprise labile linkages that are capable of being cleaved under specific physiological conditions including, for example, pH, presence of enzymatic activity, oxidizing or reducing conditions, presence of nucleophiles, etc. Suitable linkers comprise functional groups such as amides, carbamates, thiocarbamates, oxygen esters, thioesters, glycolate esters, lactate esters, orthoesters, acetals, ketals, phosphodiesters, disulfides, and mixtures thereof. In a particular embodiment, the linkers are capable of unmasking an element selected from the group consisting of binding elements and transport elements. The linker between the recognition element or elements and the hydrophilic element can be any covalent linkage, and can be stable or cleavable under physiological conditions.

In another embodiment, the present invention provides oligomers, polymers, and/or mixtures thereof having a recognition element or elements which are covalently attached to at least one reactive chemical group or reactive linker, wherein the reactive chemical group or the reactive linker is capable of reacting with at least one functional group on the protein drug, and wherein the reactive chemical group or reactive linker is capable of forming at least one covalent linkage between the recognition element or elements and the protein drug. Examples of such reactive chemical groups are known in the art, and are used for the covalent modification of proteins. Suitable reactive chemical groups include active esters, activated disulfides, maleimide derivatives, photoreactive groups, and others. These reactive chemical groups form covalent linkages with functional groups on the protein such as amino, hydroxyl, thiol, and other groups.

As a result of the formation of a covalent linkage to the protein, the oligomer, polymer or mixtures thereof will be even more tightly bound to the protein than with a purely noncovalent interaction, thus further increasing the durability of the complex. It is also possible that the covalent linkage thus formed, or other parts of the chemical moiety that is interposed between the original recognition element and the protein, may be cleavable under physiological conditions.

In a particular embodiment, the oligomers, polymers, and/or mixtures thereof further comprise at least one linker that is capable of being cleaved under physiological conditions. Suitable linkers comprise functional groups such as amides, carbamates, thiocarbamates, oxygen esters, thioesters, glycolate esters, lactate esters, orthoesters, acetals, ketals, phosphodiesters, disulfides, and mixtures thereof.

The complex of this invention comprises at least one oligomer or polymer and a protein drug, wherein the oligomer or polymer comprises at least one recognition element covalently attached to a hydrophilic element, wherein the recognition element or elements interact noncovalently with the protein drug to form a complex in which the protein drug is protected from degradation, recognition by the immune system, and/or renal excretion. In a particular embodiment, when the protein drug has an active site, the active site is not obstructed by the oligomer or polymer, thereby maintaining biological activity of the protein drug in the complex. In another embodiment, the complex has a plurality of recognition elements, wherein each recognition element binds to a mutually distinct site on the protein drug, which may be produced by using branched architecture offering multiple chain ends. Alternatively, a plurality of recognition elements may be distributed throughout linear or branched hydrophilic elements at discrete locations.

FIGS. 6-9 show methods for the discovery of recognition elements suitable for the invention that can be incorporated into hydrophilic copolymers of a structure depicted in FIG. 5, which can subsequently be formulated with proteins to generate protected proteins useful as drugs. The methods described here rely upon the use of phage display techniques (Nilsson, et al., *Adv. Drug Deliv. Rev.* 2000, 43, 165; U.S. Pat. No. 5,622,699), but those skilled in the art of ligand generation will be able to devise other methods of finding peptide or non-peptide ligands, e.g. by combinatorial chemical methods in which the potential ligand libraries are displayed on a surface or resin beads for assay screening or selection, and may further be displayed in an arrayed fashion to aid this process, as mentioned above. Other schemes for finding peptide ligands utilizing phage-display techniques may also be devised by those skilled in the art.

Phage display techniques for the discovery of ligands offer the advantage of ready generation of diverse libraries, and ease of selection for binding using resin-based strategies. Positive and negative (i.e. subtraction) selections are possible. It is also possible with these techniques to generate families of ligands that bind with any desired affinity for their binding sites by gradually increasing the stringency of their elution. This can be achieved by increasing the concentration of a denaturant, increasing or decreasing the ionic strength, changing the pH of the buffer, changing the proportion of an organic cosolvent, etc. in a gradual or stepwise fashion, such that ligands of low affinity can be eluted first, followed by ligands of medium affinity, and finally by those of the highest affinity.

Figure 6:
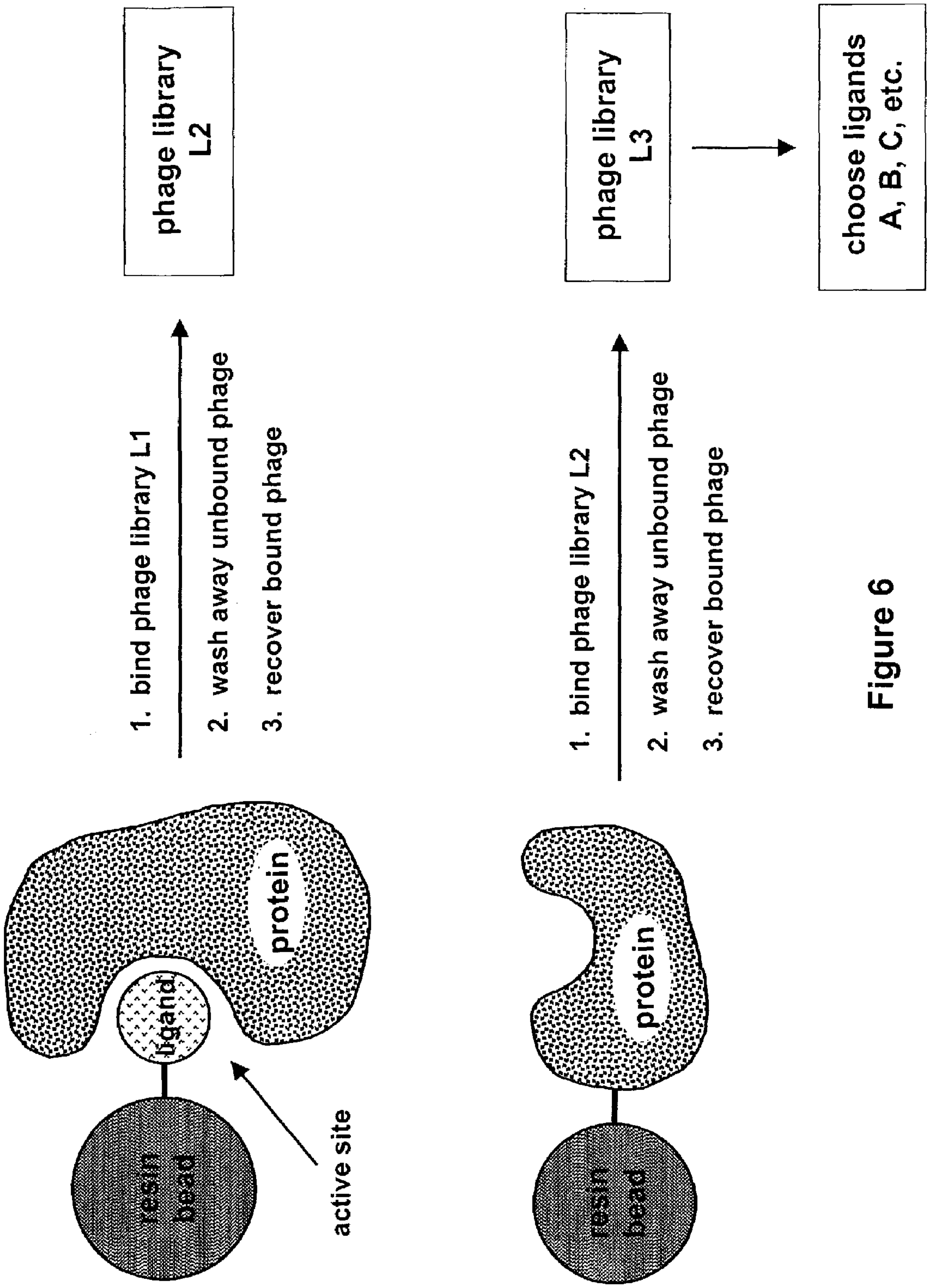
FIG. 6: Schematic drawing depicting a method for the discovery of ligands (A, B, C, etc.) that bind to a protein at sites other than its active site. Shown is a protein, which binds to a ligand via its active site. The ligand is covalently attached to a resin bead, and the protein is added so as to form a complex between the protein and the ligand on the surface of the resin bead. The complex is then exposed to a phage library L1 under conditions allowing the phage-displayed ligands to bind to the protein. Unbound phage are washed away, and then bound phage are released and eluted under suitable conditions, to generate phage library L2. Next, resin-bound protein, in the absence of bound ligand, is exposed to phage library L2 under conditions allowing ligands displayed on the phage to bind to the protein. Unbound phage are washed away, and bound phage are released and eluted under suitable conditions to generate phage library L3. From inspection of similarities and differences among the sequences of ligands recovered in library L3, ligands A, B, C, etc. that bind to mutually distinct sites on the protein are chosen.

The simplest mode in which ligands for a protein can be discovered with phage display techniques is shown in FIG. 6. The success of this mode depends upon the ability to discern which ligands selected from a library actually bind to mutually distinct sites on a protein by simple inspection and comparison of their sequences. As shown in FIG. 6, a protein with a single active site is complexed with its active-site ligand, which has previously been covalently or noncovalently linked to a resin bead. Unbound protein is washed away, after which the resin-bound complex is exposed to phage library L1, under conditions that allow the phage-displayed ligands to bind to sites on the protein. Unbound phage are washed away, and the bound phage are released and eluted under suitable conditions (e.g. change in ionic strength, pH, temperature, solvent composition, denaturing agents, surfactants, etc.) to generate phage library L2. The protein without a bound active-site ligand is then covalently or noncovalently linked to a resin bead, and is exposed to library L2 under conditions which allow the phage-displayed ligands to bind to the protein. Unbound phage is washed away, and bound phage are then released and eluted under suitable conditions to generate phage library L3. The sequences of the ligands from library L3 are inspected and compared to determine which sequences bind to mutually distinct sites based upon similarities and differences in their sequences. Ligands A, B, C, etc. that bind to mutually distinct sites are chosen based on this analysis.

If it is not possible to readily discern by inspection of ligand sequences those which bind to mutually distinct sites on a protein, other methods may be employed to find such ligands sequentially. Two cases are described here in detail. The first case involves the discovery of ligands that bind to mutually distinct binding sites that are not the active site, for a protein having a single active site.

Figure 7A:
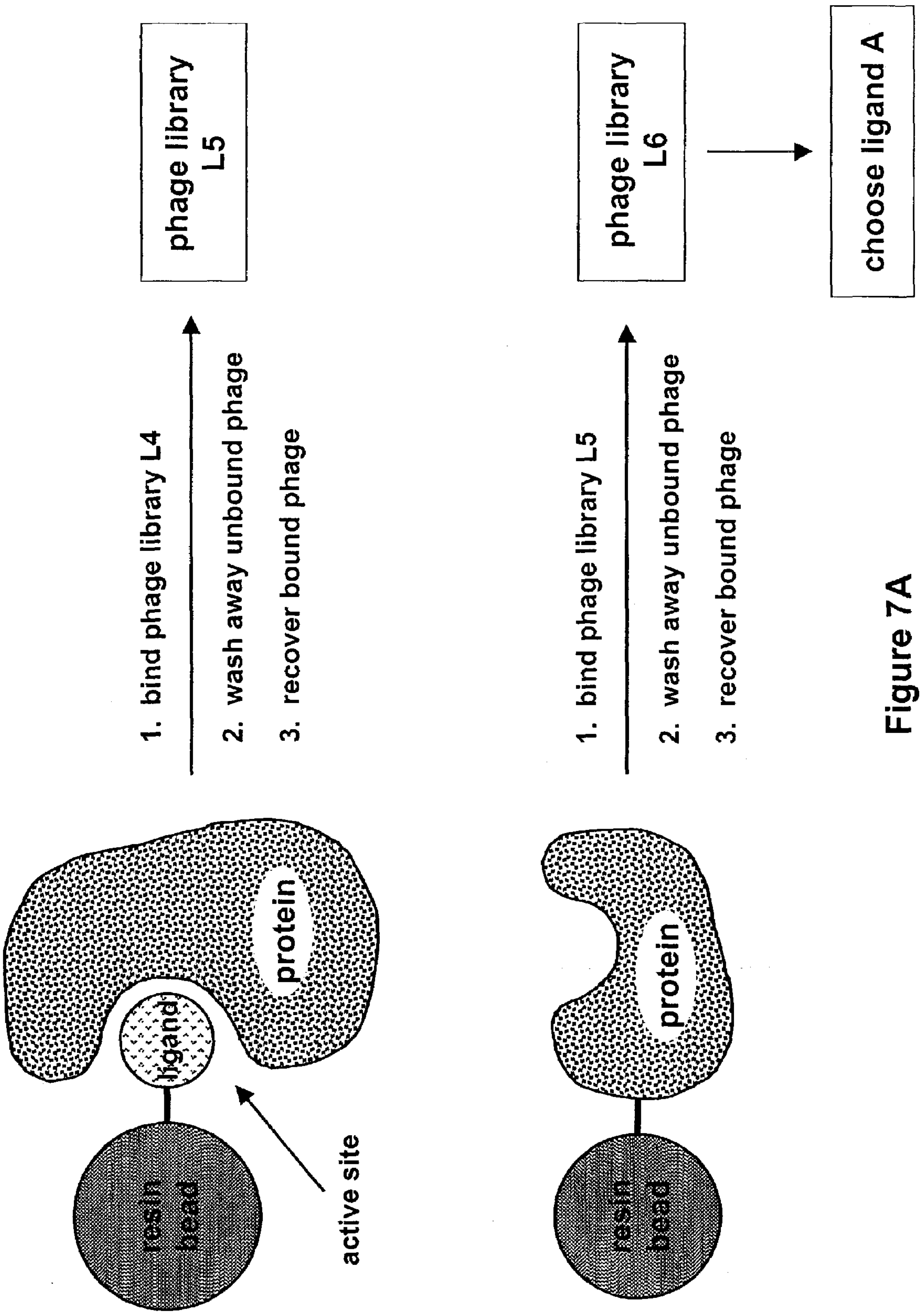
FIG. 7A: Schematic drawing depicting a method for the discovery of a ligand (ligand A) that binds to a protein at a site other than its active site. Shown is a protein, which binds to a ligand via its active site. The ligand is covalently attached to a resin bead, and the protein is added so as to form a complex between the protein and the ligand on the surface of the resin bead. The complex is then exposed-to a phage library L4 under conditions allowing the phage-displayed ligands to bind to the protein. Unbound phage are washed away, and then bound phage are released and eluted under suitable conditions, to generate phage library L5. Next, resin-bound protein, in the absence of bound ligand, is exposed to phage library L5 under conditions allowing ligands displayed on the phage to bind to the protein. Unbound phage are washed away, and bound phage are released and eluted under suitable conditions to generate phage library L6. A single sequence, designated "ligand A," is chosen from the sequences of ligands recovered in library L6.

As shown in FIG. 7A, such a protein is complexed with its active-site ligand, which has previously been covalently or non-covalently linked to a resin bead. Unbound protein is washed away, after which the resin-bound complex is exposed to phage library L4, under conditions that allow the phage-displayed ligands to bind to sites on the protein. Unbound phage are washed away, and the bound phage are released and eluted under suitable conditions (e.g. change in ionic strength, pH, temperature, solvent composition, denaturing agents, surfactants, etc.) to generate phage library L5. The protein without a bound active-site ligand is then covalently or noncovalently linked to a resin bead, and is exposed to phage library L5 under conditions, which allow the phage-diplayed ligands to bind to the protein. Unbound phage is washed away, and bound phage are then released and eluted under suitable conditions to generate phage library L6. A single sequence, designated “ligand A,” is chosen from the sequences of ligands recovered in library L6.

Figure 7B:
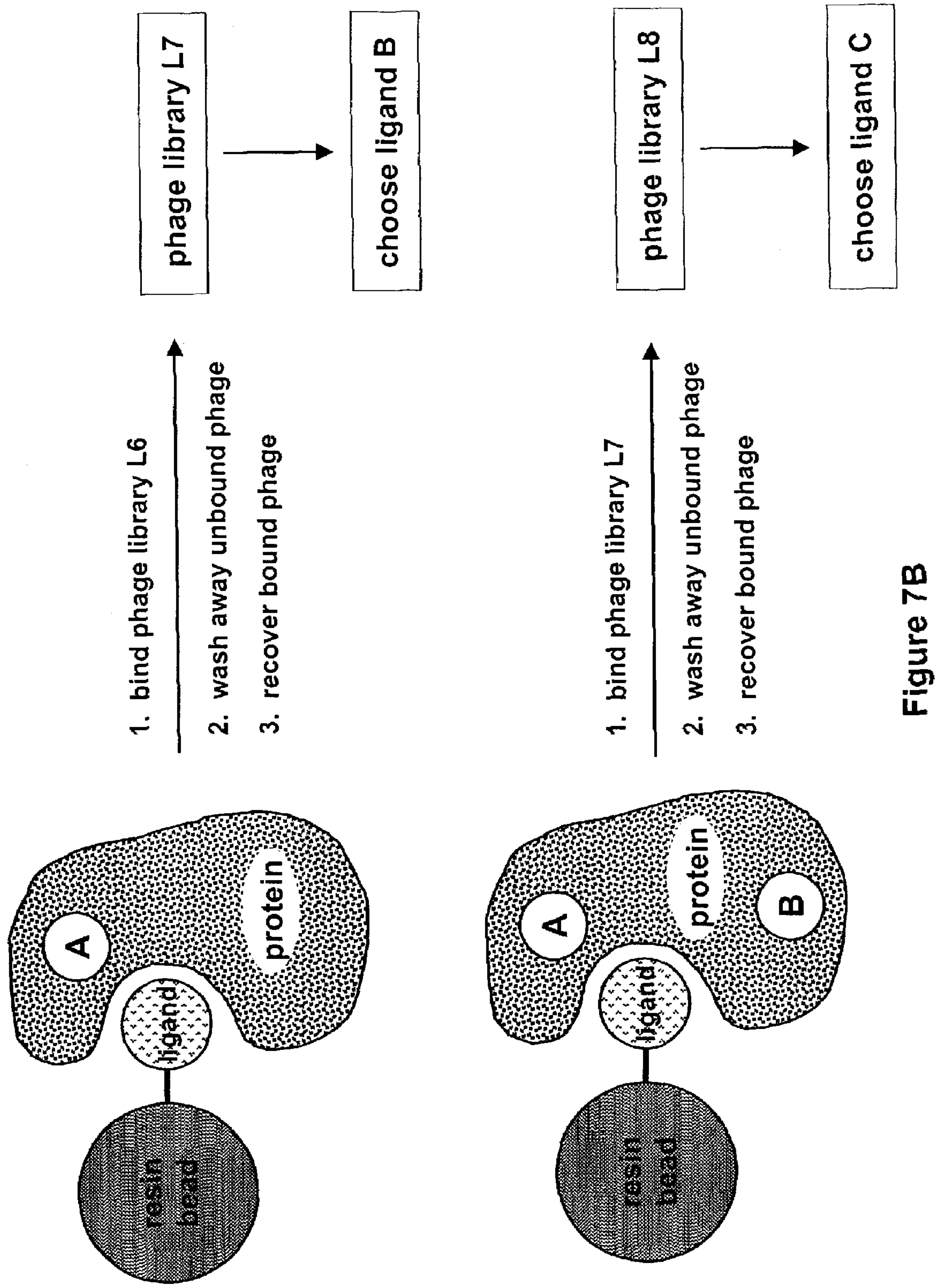
FIG. 7B: Schematic drawing depicting a method for the discovery of a second and third ligand (ligands B and C, respectively), that have mutually distinct binding sites, and do not bind to the active site. First, a complex is formed between the protein and its active-site ligand, which is covalently attached to a resin bead. Ligand A (derived as in FIG. 7A) is added under conditions which allow it to bind to the protein, but which do not disrupt the binding of the active-site ligand to the protein, and unbound ligand A is washed away. The complex thus formed is exposed to phage library L6 under conditions that allow phage-displayed ligands to bind to the protein. Unbound phage are washed away, and bound phage are then released and eluted under suitable conditions to generate phage library L7. A single sequence, designated "ligand B," is chosen from library L7. To discover a third ligand, ligands A and B are added to a complex already formed between the protein and its resin-bound active-site ligand, under conditions that allow ligands A and B to bind to the protein. Unbound ligands A and B are washed away, and the complex so formed is then exposed to phage library L7, under conditions that allow phage-displayed ligands to bind to the protein. Unbound phage are washed away, and bound phage are then released and eluted under suitable conditions to generate phage library L8. A single sequence, designated "ligand C," is chosen from library L8.

The discovery of an additional ligand B, which does not bind to the active site or the binding site of ligand A, and ligand C, which does not bind to the active site, or the binding sites of ligands A and B, is depicted in FIG. 7B. A complex is formed between the protein and its resin-bound active site ligand as described above. Next, ligand A is added to the complex in excess under conditions that allow it to bind to its binding site, and unbound ligand A is washed away to form the complex shown in the upper left of FIG. 7B. Alternatively, ligand A could be linked to a bulky moiety to provide additional steric hindrance of its binding site. This complex is then exposed to phage library L6, under conditions that allow the phage-displayed ligands to bind to the protein. Unbound phage are washed away, and bound phage are released and eluted under suitable conditions to generate phage library L7. A single sequence, designated “ligand B,” is chosen from library L7.

Again a complex is formed between the protein and its resin-bound active site ligand as described above. Ligands A and B are added in excess under conditions that allow them to bind to their respective binding sites, and then unbound ligands A and B are washed away to form the complex depicted at the lower left of FIG. 7B. Alternatively, ligands A and B could individually be linked to bulky moieties to provide additional steric hindrance of their binding sites. This complex is exposed to phage library L7 under conditions that allow the phage-displayed ligands to bind to the protein. Unbound phage are washed away, and the bound phage are then released and eluted under suitable conditions to generate phage library L8, from which a single sequence is chosen, designated “ligand C.”

Additional ligands D, E, F, etc. that have mutually distinct binding sites can be discovered, if desired, by iterating the above procedure. Note that an alternative method to the one above can be employed in which the protein is directly attached covalently or non-covalently to the resin support, rather than the active-site ligand. In this case, the free active-site ligand would be added to the resin-bound protein to form the complex used for phage selection.

Figure 8A:
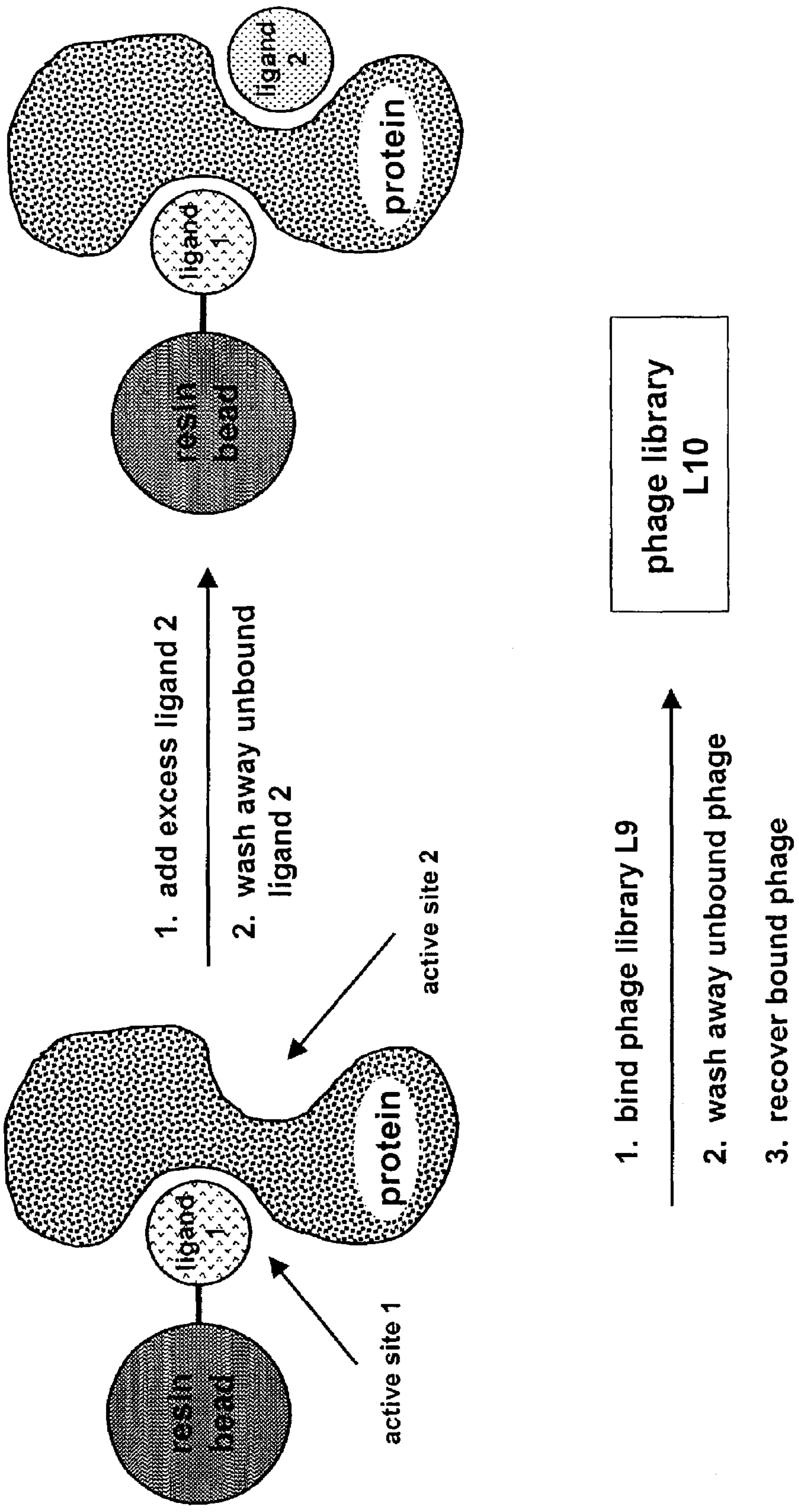
FIG. 8A: Schematic drawing depicting the discovery of a ligand (ligand X), that binds to a protein at a site other than the active site, in the case where the protein contains two active sites. First, the ligand for active site 1 (ligand 1) is attached covalently to a resin bead. Next, the protein is allowed to bind to the resin-bound ligand 1 under suitable conditions, and excess protein is washed away. Then an excess of ligand 2 (which is the same or different from ligand 1, but binds to active site 2, and has similar or lesser affinity for active site 2 than ligand 1 has for active site 1), is added to the complex, under conditions which allow ligand 2 to bind to active site 2, without disrupting the interaction of ligand 1 with active site 1. Unbound ligand 2 is then washed away, and the resulting complex is exposed to phage library L9 under conditions that allow phage-displayed ligands to bind to the protein. Unbound phage are washed away, and the bound phage are released and eluted under suitable conditions, to generate phage library L10.

A second case for the sequential discovery of ligands with mutually distinct binding sites, which do not bind to the active site involves a protein having two active sites. One active site, designated active site 1, is bound by ligand 1, and the second active site, designated active site 2, is bound by ligand 2. Ligand 1 and ligand 2 may be the same or different, and the affinities of ligands 1 and 2 for their active sites may be the same or different. As shown in FIG. 8A, ligand 1 is bound covalently or noncovalently to a resin bead, and the protein is added in excess under conditions that allow the ligand to bind to active site 1. Unbound protein is washed away, and then ligand 2 is added in excess under conditions that allow ligand 2 to bind to active site 2, while allowing ligand 1 to remain bound to active site 1. Unbound ligand 2 is washed away to form the complex shown in the upper right of FIG. 8A. This complex is exposed to phage library L9 under conditions, which allow the phage-displayed ligands to bind to the protein. Unbound phage are washed away, and the remaining bound phage are released and eluted under suitable conditions to generate phage library L10.

Figure 8B:
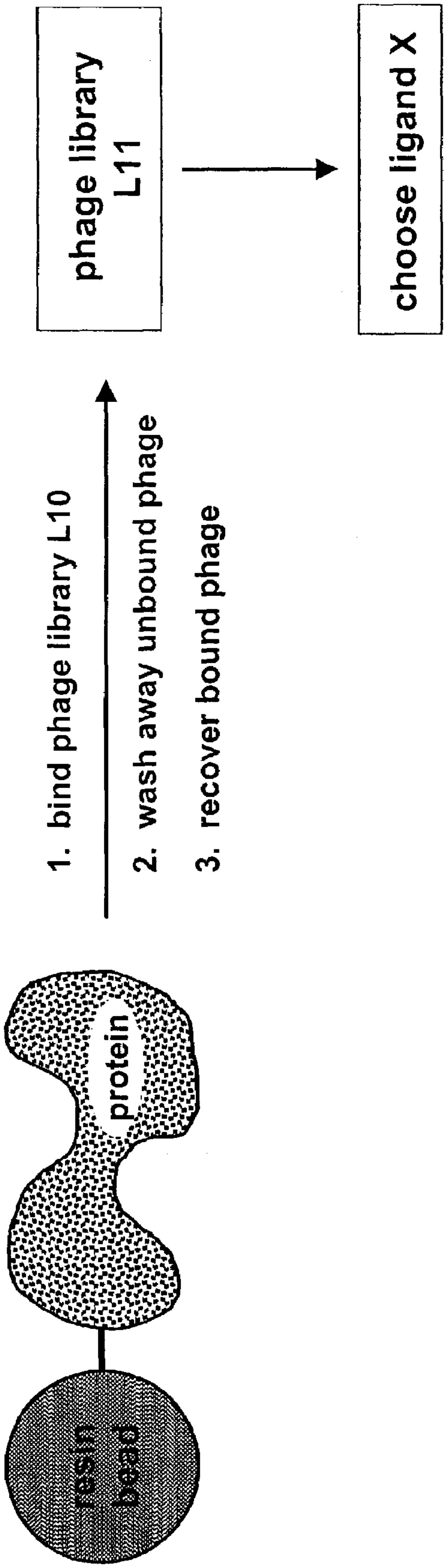
FIG. 8B: Schematic drawing depicting the discovery of a ligand (ligand X), that binds to a protein at a site other than the active site, in the case when the protein contains two active sites. The protein from FIG. 8A, without active site ligands bound, is covalently attached to a resin bead, and then exposed to phage library L10 under conditions that allow phage-displayed ligands to bind to the protein. Unbound phage are washed away, and the bound phage are released and eluted under suitable conditions to generate phage library L11. A single sequence, designated "ligand X," is chosen from library L11.

As shown in FIG. 8B, the protein without bound active site ligands is covalently or noncovalently attached to a resin bead. The resin bound protein is exposed to phage library L10 under conditions that allow the phage-displayed ligands to bind to the protein. The unbound phage are washed away, and the remaining bound phage are released and eluted under suitable conditions to generate phage library L11. A single sequence, designated "ligand X," is chosen from library L11.

By repeating this procedure in a fashion similar to that described above for the case of a protein with a single active site, additional ligands Y, Z, etc. can be discovered such that they do not bind to the active sites of the protein, and that ligands X, Y, Z, etc. have mutually distinct binding sites. An alternative method to the one above can be employed in which the protein is directly attached covalently or non-covalently to the resin support, rather than the active-site ligand. In this case, the free active-site ligand would be added to the resin-bound protein to form the complex used for phage selection.

The ligands A, B, C, etc, and X, Y, Z, etc. generated using the above procedures can be utilized as the recognition elements of the hydrophilic copolymer of this invention. Those skilled in the art of ligand generation can devise alternative means to identify A, B, C, etc. and X, Y, Z, etc., including methods not involving phage display techniques. All such identified ligands shall be equally useful for incorporation as the recognition elements of the hydrophilic copolymers of FIG. 5. As described above, each can be covalently linked to the hydrophilic element, either as individual ligands, or in a repeated fashion as multivalent ligands to increase their affinity for their respective binding sites.

Figure 9A:
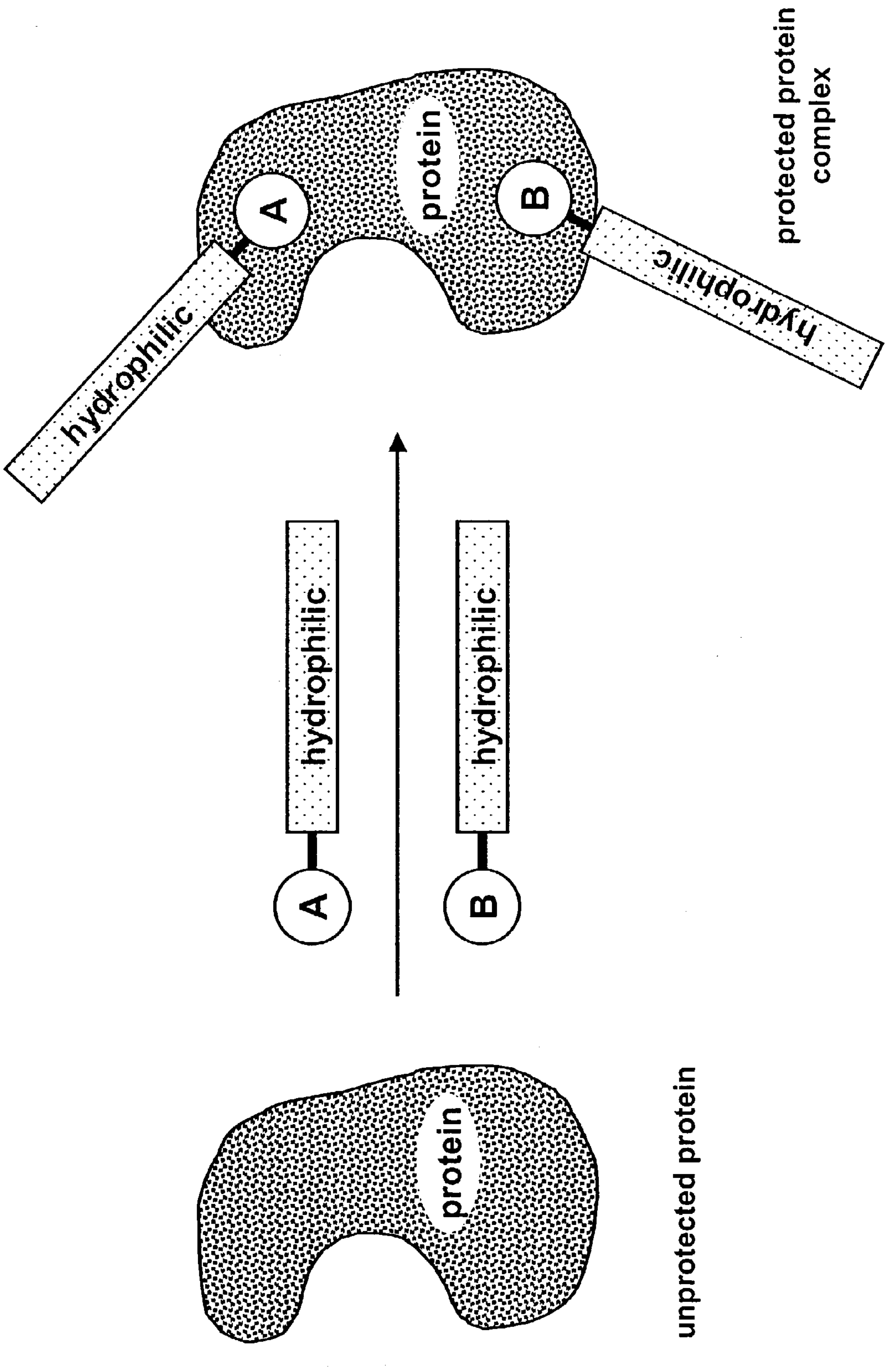
FIG. 9A: Schematic drawing depicting a method for protecting a protein with a hydrophilic copolymer comprising a hydrophilic element covalently linked to a recognition element. Two different such copolymers, one which comprises ligand A as the recognition element covalently linked to a hydrophilic element, and the other comprising ligand B as the recognition element covalently linked to a hydrophilic element, are added to the protein under conditions which permit the noncovalent interaction of the ligands A and B with their binding sites on the protein. A stoichiometric amount or a slight excess of the copolymers is added. The ligands A and B in these copolymers bind to the protein at mutually distinct sites that are also not the active site of the protein, forming a complex. The protein is thereby protected from degradation by enzymes, recognition by the immune system, or renal excretion, while remaining able to bind its active-site ligand.
Figure 9B:
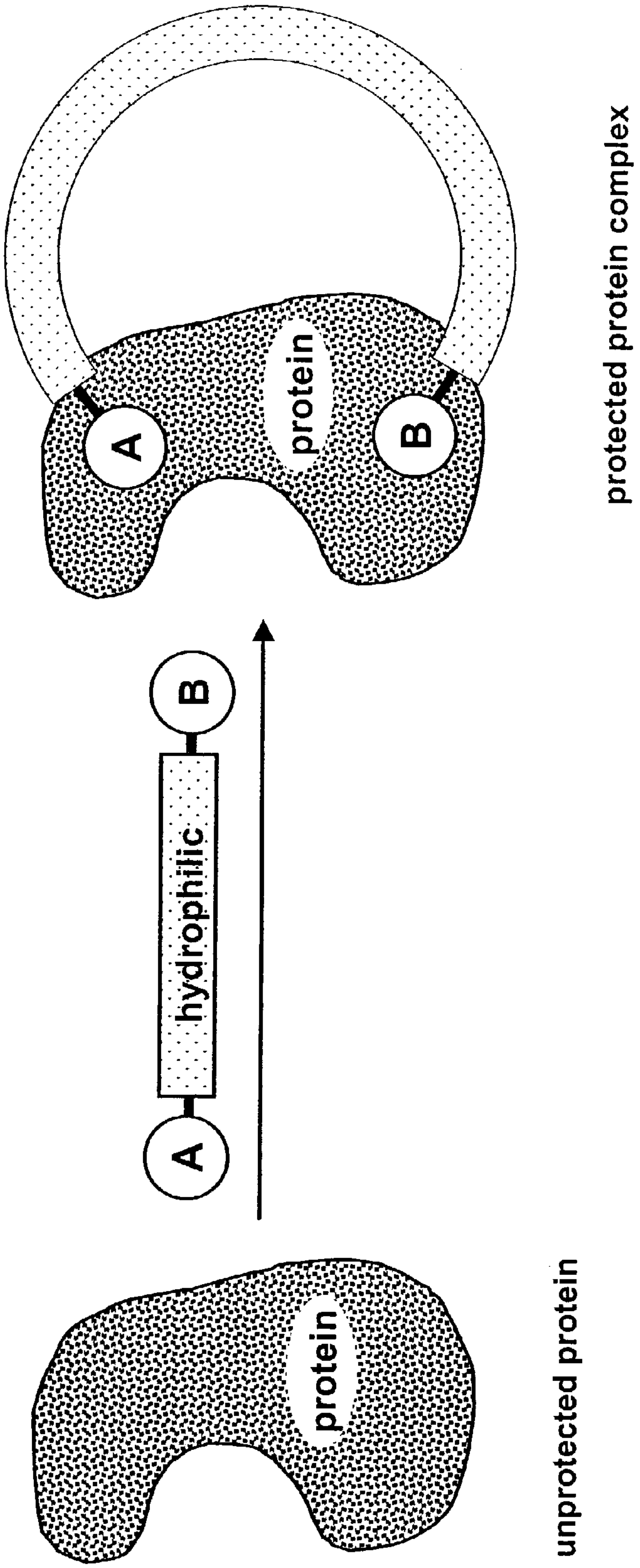
FIG. 9B: Schematic drawing depicting a method for protecting a protein with a hydrophilic copolymer comprising a hydrophilic element covalently linked to two different recognition elements. One copolymer is synthesized, comprising a hydrophilic element covalently linked at one end to ligand A, and covalently linked at the other end to ligand B, where ligands A and B function as recognition elements that bind to mutually distinct sites on the protein that are also not the active site. The copolymer is added to the protein under conditions that permit the noncovalent interaction of the ligands A and B with their binding sites on the protein. A stoichiometric amount or a slight excess of the copolymer is added. A complex is formed between the copolymer and the protein in which the hydrophilic element of the copolymer forms a looping structure, thereby protecting the protein from degradation by enzymes, recognition by the immune system, or renal excretion, while remaining able to bind its active-site ligand.

FIGS. 9A and 9B show how these copolymers could be used to generate a protected protein. Shown in FIG. 9A is a protein with a single active site, for which two ligands, A and B, with mutually distinct binding sites, which also do not bind the active site, are each linked covalently to different hydrophilic elements. Both the protein and the hydrophilic copolymers can be rigorously purified before formulation. Both hydrophilic copolymers are mixed with the protein in an aqueous solution under conditions which allow the ligands to bind to their binding sites on the protein, generating a complex in which the hydrophilic copolymers are bound to the protein noncovalently.

Shown in FIG. 9B is another means to protect the protein utilizing ligands A and B. In this case, the ligands A and B are linked covalently to opposite ends of the same hydrophilic element. Again, both the protein and the hydrophilic copolymer can be rigorously purified before formulation. The hydrophilic copolymer is mixed with the protein in an aqueous solution under conditions which allow the ligands to bind to their binding sites on the protein, generating a complex in which the hydrophilic copolymer is noncovalently bound to the protein at the ends, with the hydrophilic element forming a looping structure in between.

Complexes such as those depicted in FIGS. 9A and 9B protect the protein from degradation, renal excretion, and immune recognition, and since the active site of the protein is unhindered, its biological activity is preserved. There is no need for further purification of the protein/hydrophilic copolymer complex. Inclusion of cleavable linkers, and/or masked or unmasked binding elements or transport elements within the hydrophilic element, as described earlier, may further enhance the potency of the therapeutic protein at the site of action.

Although this invention has been described with respect to certain specific embodiments, it will be appreciated by those skilled in the art that various modifications may be made without departing from the spirit and scope of the invention. The present invention is further illustrated by the following examples.

EXAMPLES

Example 1

Synthesis of a Peptide-oligosaccharide Conjugate Using a Carbamate Linker as a Smart Surfactant for the Encapsulation of Hydrophobic Drugs A peptide tetramer, consisting of 4 phenylalanine residues, is synthesized on Rink amide resin using standard Fmoc chemistry. After removal of the final Fmoc group, cleavage from the resin with 95:5 TFA/water liberates the peptide with a C-terminal carboxamide and a free α-amino group. An oligosaccharide is synthesized using an acceptor-bound glycosylation strategy on Merrifield resin employing a photocleavable linker. The first glycosyl donor is coupled to the hydroxyl-bearing linker at its anomeric carbon. Acetyl groups are used for temporary protection of the primary hydroxyl acceptor groups, cleavable after each coupling step with DBU; all other hydroxyl groups are protected as their benzyl ethers. After coupling of the final glycosyl donor, the final acetyl group is removed with DBU, and the resulting free primary hydroxyl group is activated with alkaline cyanogen bromide. An excess of the peptide tetramer is added and allowed to react with the activated resin-bound oligosaccharide in the presence of a hindered organic base, resulting in the formation of a carbamate linkage between the peptide and the oligosaccharide. Unreacted peptide is washed away, and the benzyl-protected peptide-oligosaccharide conjugate is cleaved from the resin by irradiation with light. The benzyl protecting groups are removed by catalytic hydrogenation, and the fully deprotected conjugate is purified to homogeneity by HPLC.

Example 2

Synthesis of a Peptide-oligosaccharide Conjugate Using an Amide Linker as a Smart Surfactant for the Encapsulation of Hydrophobic Drugs A peptide pentamer, consisting of 5-tryptophan residues in which the side chain indole nitrogens are protected as tert-butylcarbamates, is synthesized on Rink amide resin using standard Fmoc chemistry. After the final coupling reaction, the terminal Fmoc group is removed, leaving the protected peptide with a free amino group attached to the resin. An oligosaccharide is synthesized using an acceptor-bound glycosylation strategy on Wang resin. The first glycosyl donor is coupled to the hydroxyl-bearing linker at its anomeric carbon. Acetyl groups are used for temporary protection of the primary hydroxyl acceptor groups, cleavable after each coupling step with DBU; all other hydroxyl groups are protected as their benzyl ethers. The final glycosyl donor is a derivative of glucuronic acid in which the carboxylic acid group is protected as its tert-butyl ester, and the hydroxyl groups are protected as their benzyl ethers. After coupling of the final glycosyl donor, the resin bound intermediate is treated with 95:5 TFA/water, releasing the benzyl-protected oligosaccharide with a free carboxylic acid group at one terminus and a free anomeric hydroxyl group at the other terminus. The carboxylic acid group of the protected oligosaccharide is activated by treatment with HBTU and DIEA, and then added to the resin-bound, side-chain-protected tryptophan pentamer, and allowed to react with it to form an amide bond. Excess activated oligosaccharide is washed away, and the protected peptide-oligosaccharide conjugate is cleaved and partially deprotected by treatment with 95:5 TFA/water. The remaining benzyl groups are removed by catalytic hydrogenation, and the completely deprotected peptide-oligosaccharide conjugate is purified to homogeneity by HPLC.

Example 3

Synthesis of a Branched Peptoid as a Smart Surfactant for the Encapsulation of Hydrophobic Drugs Using a Fmoc-based monomer strategy, a tetrameric peptoid with 2-phenethyl side chains is synthesized on Rink amide resin, using HBTU/DIEA activation. After removal of the final Fmoc, three peptoid residues are added containing a side-chain mannosyl C-glycoside with isopropylidine-protected hydroxyl groups. Next, a symmetrical linker containing one free carboxyl group and two primary amino groups protected with Fmoc groups is activated with HBTU/DIEA, and coupled to the resin-bound peptoid. After removal of the Fmoc groups, five peptoid residues containing a side-chain mannosyl C-glycoside with isopropylidine-protected hydroxyl groups are added to each amino group in succession to generate a branched structure. The final Fmoc groups are removed, and the N-terminal secondary amines are acetylated with acetic anhydride/pyridine in DMF. The resin is treated with 95:5 TFA/water, to cleave the peptoid and remove the protecting groups. The deprotected peptoid is purified to homogeneity by HPLC.

Example 4

Synthesis of a Peptoid with Side Chains of Gradually Increasing Size as a Smart Surfactant for the Encapsulation of Hydrophobic Drugs Using a Fmoc-based monomer strategy, a pentameric peptoid with indole-containing side chains, in which the indole nitrogens are protected as their t-butylcarbamates, is synthesized on Rink amide resin, using HBTU/DIEA activation. After removal of the final Fmoc, three peptoid residues are added containing a side-chain monosaccharide with isopropylidine-protected hydroxyl groups. Next, three peptoid residues are added containing a side-chain disaccharide with isopropylidine-protected hydroxyl groups. Finally, three peptoid residues are added containing a side-chain trisaccharide with isopropylidine-protected hydroxyl groups. The final Fmoc group is removed, and the N-terminal secondary amine is acetylated with acetic anhydride/pyridine in DMF. The resin is treated with 95:5 TFA/water, to cleave the peptoid and remove the protecting groups. The deprotected peptoid is purified to homogeneity by HPLC.

Example 5

Intravenous Delivery of a Hydrophobic Small Molecule Drug

Drug “M” is a hydrophobic small molecule drug that is poorly soluble in aqueous media. A smart surfactant can be synthesized in which the hydrophobic element is comprised of a peptide with aromatic side chains, and the hydrophilic element is comprised of an oligosaccharide. The oligosaccharide is attached to the peptide by means of a short noncleavable linker. Drug M is combined with the smart surfactant in an aqueous buffer and the mixture is agitated to form a nearly monodisperse population of micelles each containing a nanoparticle of the drug. Dextrin is added to this suspension, and the mixture is then lyophilized to produce a powder with an adequate shelf life. Immediately prior to administration, the powder is resuspended in sterile phosphate buffered saline (PBS) at pH 7.5, and delivered intravenously. The solublized drug circulates throughout the bloodstream, and intact surfactant molecules are gradually shed from the micelle, exposing drug M, which then travels to its site of action via low affinity binding to serum albumin.

Example 6

Intravenous Delivery of Cyclosporin A to the CNS for the Regeneration of Damaged Neurons Cyclosporin A is a hydrophobic drug that is poorly soluble in aqueous media. A smart surfactant, designed to encapsulate hydrophobic drugs, can be synthesized such that L-glutamate is covalently linked to the free end of the hydrophilic element as a ligand. Within the hydrophilic element is a labile thioester linkage positioned in the middle of the hydrophilic element. Cyclosporin A is combined with this smart surfactant in an aqueous buffer, and gentle agitation is applied to generate a nearly monodisperse population of micelles containing a drug nanoparticle of 15 nm average diameter. Glucose is added to the aqueous suspension of micelles, which is then lyophilized to produce a powder with an adequate shelf life. Just prior to administration, the powder is dissolved in sterile PBS at pH 7.5, and delivered intravenously to the patient. The solublized drug circulates throughout the bloodstream, and the L-glutamate ligand binds to receptors in the blood brain barrier, localizing the drug-containing micelles. Gradual hydrolysis of the thioester linkage causes the hydrophilic element to decompose, resulting in the uncoating of the cyclosporin A nanoparticle, which is deposited at the same location. Cyclosporin A then crosses the blood brain barrier by diffusion through the membranes of the epithelial cells to reach the interstitial fluid of CNS.

Example 7

Intravenous Delivery of Cyclosporin A to the CNS for the Regeneration of Damaged Neurons This example is the same as Example 6, except that the hydrophilic element, upon decomposition, is converted into a permeation enhancing agent, which then increases the permeability of the epithelial barrier to the passage of cyclosporin A.

Example 8

Intravenous Delivery of Methotrexate to the CNS for the Treatment of Brain Cancer Methotrexate is an anticancer drug that is hydrophilic, and thus unable to cross the blood brain barrier. Methotrexate is covalently linked, via a cleavable traceless linker to the PLE of a smart surfactant for the formation of a polar-core micelle. Contained within the hydrophilic element of the surfactant is a glycolate ester linkage positioned in the middle of the hydrophilic element. At the free end of the hydrophilic element a ligand containing a 1,4 dihydronicotinamide moiety is present, attached via a covalent linkage. The methotrexate-smart surfactant conjugate is added to an aqueous buffer at pH 3 and gentle agitation is applied to generate a nearly monodisperse population of polar-core micelles of 35 nm average diameter. Dextrin is added to this suspension, and it is lyophilized to produce a powder with an adequate shelf life. Just prior to administration, the lyophilized powder is resuspended in sterile PBS pH 7.5 and delivered to the patient intravenously. The micelle-encapsulated methotrexate circulates throughout the bloodstream, and the 1,4 dihydronicotinamide moiety binds to receptors in the blood brain barrier. Receptor-mediated transcytosis occurs, transporting the polar-core micelles containing methotrexate into the interstitial fluid of the brain. Gradual hydrolysis of the glycolate ester linkages causes the hydrophilic element of the micelles to decompose, resulting in the disassembly of the micelles. Exposure of the core to physiological conditions results in the cleavage of the linker that attaches the methotrexate to the PLE, causing free methotrexate to be released into the interstitial fluid of the brain.

Example 9

Intravenous Delivery of Methotrexate to the CNS for the Treatment of Brain Cancer This example is the same as Example 8, except that the hydrophilic element of the surfactant contains many masked amino groups that are protected in an uncharged state with a chemical group that breaks down gradually at physiological pH to unmask the amino groups, which become protonated and positively charged. Micelles formed from this surfactant and carrying methotrexate bind to dihydropyridine receptors of the blood brain barrier. The amino groups become unmasked at pH 7.5, and the resulting network of covalently linked positive charges increases the permeability of the barrier by the paracellular route. Concomitant decomposition of the hydrophilic element due to gradual cleavage of the glycolate ester causes the methotrexate cargo to be released, which then moves through the blood brain barrier via the paracellular route into the interstitial fluid of the brain.

Example 10

Intravenous Delivery of Erythropoietin Protected by Hydrophilic Copolymers

Using the phage-display methods described in the invention for a protein with two active sites, two ligands for EPO, R and S, are discovered that have mutually distinct binding sites and do not bind to the active sites of EPO. The extracellular domain of the EPO receptor is used for both ligand 1 and ligand 2. Ligands R and S are each trimerized using a suitable covalent linker, and the trimeric ligands are then each individually attached covalently to a branched hydrophilic peptoid of a single length and structure. These conjugates are purified to near homogeneity. EPO is generated by expression in eukaryotic cells such that no oligosaccharide chains have been added post-translationally, or by chemical synthesis. The EPO so produced is also purified to near homogeneity. The hydrophilic copolymers containing R and S ligands are added to EPO in an aqueous buffer to form a stabilized complex. The solution is lyophilized to generate a powder with an adequate shelf life. Just prior to administration, sterile PBS at pH 7.5 is added to the powder, and it is redissolved. The resulting solution is administered intravenously. The stabilized EPO complex circulates in the blood stream to its target receptors, whereupon it binds those receptors. As a result, the production of red blood cells is stimulated.

Example 11

Intravenous Delivery of Cholera Toxin A Subunit to a Tumor for the Treatment of Metastasized Cancer Using the phage-display methods of the invention, two ligands F and G are discovered that bind to mutually distinct binding sites on cholera toxin A (catalytic) subunit, but do not bind to the active site. An inhibitor of cholera toxin activity is used as the active site ligand. Ligands F and G are individually linked covalently to branched oligosaccharides of a defined single length and composition, which also contain ester linkages that are substrates for esterases present in blood serum. The hydrophilic copolymers so produced are purified to near homogeneity, and are added to a buffered aqueous solution at pH 7 containing purified cholera toxin A subunit, thereby forming a stabilized protein complex. To this solution is added a smart surfactant whose PLE contains chemical groups of charge opposite to the net surface charge of the cholera toxin A subunit at pH 7. The hydrophobic element of the smart surfactant contains an $\alpha$-helical peptide with hydrophobic side chains. One-third of the way through the hydrophobic peptide sequence are interposed three asparagine residues, which have the effect of forcing the surfactant chains to align in a parallel fashion by hydrogen bonding to asparagine side chains in the hydrophobic elements of adjacent surfactant molecules. Attached covalently at the end of the hydrophilic element is a synthetic ligand that binds with high selectivity to subtype 2 somatostatin receptors overexpressed on tumor cells. The hydrophilic element also contains a disulfide linkage within its chain. The solution is agitated mechanically to form nearly monodisperse polar-core micelles containing the protected cholera toxin complex at its core. The micellar suspension is dialyzed to remove unencapsulated cholera toxin complex, dextrin is added, and the suspension is lyophilized to produce a powder with an adequate shelf life. Just prior to administration, the powder is dissolved in sterile PBS pH 7.5, and is then administered intravenously. The polar-core micelles containing stabilized cholera toxin circulate in the bloodstream, and the synthetic ligands bind to somatostatin subtype 2 receptors on the surface of metastasized cancer tumor cells. Receptor-mediated endocytosis causes the micelles to enter the tumor cells, and the hydrophilic element of the micelles decomposes as the disulfide in the chain is reduced in the cancer cell cytoplasm. Decomposition of the micelle releases the protected cholera toxin A subunit, which then kills the cancer cell. Once the cancer cell is destroyed, the protected cholera toxin is exposed to esterases present in the bloodstream, which cleave the ester linkage in the hydrophilic element of the hydrophilic copolymer that protects the toxin. As a result, the hydrodynamic radius of the protected cholera toxin is dramatically reduced such that it is rapidly excreted from the bloodstream by the kidneys.

Example 12

Intravenous Delivery of a Repressor of Gene Transcription to the Cytoplasm of a Macrophage A repressor protein with a pI of 9 is added to a buffered aqueous solution at pH 7 containing a smart surfactant for the formation of polar-core micelles. The PLE of the smart surfactant contains carboxylate groups, which impart a net negative charge to the PLE at pH 7. The hydrophilic element also contains a glycolate ester linkage within its chain, and a pentavalent mannose ligand attached covalently to its free end. Due to favorable interactions between the opposite charges of the PLE and the protein at pH 7, polar-core micelles are formed with gentle agitation by a self-assembly process such that all of the repressor protein is contained within the core of the micelles, which are nearly monodisperse and have an average diameter of 50 nm. To the micellar suspension is added glucose, and it is lyophilized to produce a powder with an adequate shelf life. Just prior to administration, the powder is dissolved in sterile PBS at pH 7.5, and delivered intravenously. The micelles containing the repressor protein travel in the bloodstream until they encounter macrophages, to which they bind because of the presence of a cell-surface mannose receptor. Receptor-mediated endocytosis causes the micelles to be transported inside the cell, and the gradual decomposition of the glycolate ester linkage in the hydrophilic element of the surfactant causes the micelle to decompose. As a result, the repressor protein is released within the cellular cytoplasm, allowing it to access and bind to its target DNA operator in the nucleus, thus shutting down transcription of the target gene.

Example 13

Oral Delivery of a Hydrophobic Small Molecule Drug

Drug "N" is a hydrophobic small molecule drug that is poorly soluble in aqueous media. A smart surfactant is synthesized in which the hydrophobic element is comprised of drug N, and the hydrophilic element comprises an oligosaccharide. The oligosaccharide is attached to drug N by means of a short noncleavable linker. Drug N is combined with the smart surfactant in an aqueous buffer and the mixture is agitated to form a nearly monodisperse population of micelles each containing a nanoparticle of the drug. To this suspension is added dextrin, and the mixture is then lyophilized to produce a powder with an adequate shelf life. The powder is formulated into tablets, which are administered orally. Upon entering the stomach, the tablet breaks down, releasing the micelles into the gastric fluid. The micelles travel to the small intestine, where they are transported by transcytosis through the mucosal enterocytes into the bloodstream. Due to gradual shedding of intact surfactant molecules from the micelle, drug N is exposed, and travels to its site of action via low affinity binding to serum albumin.

Example 14

Oral Delivery of a Hydrophobic Small Molecule Drug

A hydrophobic small molecule drug "Q" lacks oral bioavailability due to its low solubility in aqueous media, and because it is a substrate for cytochrome P450 3A and P-glycoprotein in mucosal enterocytes. A smart surfactant for the delivery of hydrophobic molecules is synthesized containing a thioester linkage within the hydrophilic element. The hydrophobic element is the drug itself. Drug Q and a compound that inhibits both cytochrome P450 3A and P-glycoprotein are both added to an aqueous solution containing the smart surfactant. The mixture is agitated mechanically to generate a nearly monodisperse suspension of smart micelles containing drug Q and the inhibitor at the core. Glucose is added to the suspension, and it is lyophilized to produce a powder with an adequate shelf life. The powder is formulated into tablets. The drug is administered orally in tablet form and the tablet breaks down in the stomach to release the micellar emulsion. The micelles travel through the stomach and enter the small intestine, where the increase in pH to 7.2 causes hydrolysis of the thioester, unmasking a thiol group, which causes the micelle to adhere to the mucin layer of the small intestine. The breakdown of the hydrophilic element due to hydrolysis of the thioester causes drug Q and the inhibitor to be released. Drug Q and the inhibitor permeate the apical membrane of the mucosal enterocytes, and the inhibitor inhibits the activity of cytochrome P450 3A and P-glycoprotein. Drug Q is therefore able to traverse the enterocytes intact and permeate the basolateral membrane of the enterocytes, thus entering the bloodstream.

Example 15

Oral Delivery of Insulin by Transcytosis

Insulin is conjugated to the PLE of a smart surfactant for the formation of polar-core micelles with a traceless cleavable linker attached to the tyrosine aromatic hydroxyl group of insulin. The hydrophobic element of the smart surfactant is comprised of a hydrophobic peptoid oligomer. The hydrophilic element contains an ester linkage, which is a substrate for intestinal lipases, such that cleavage of this linker will unmask a pentavalent monosaccharide ligand of a lectin found on the surface of mucosal enterocytes of the small intestine. A buffered aqueous solution at pH 4.5 containing the smart surfactant with insulin linked covalently to its PLE is agitated mechanically to generate nearly monodisperse polar-core micelles with the insulin contained in the core. Glucose is added to this suspension, and the suspension is then lyophilized to generate a powder with a long shelf life. The powder is formulated into tablets. The tablets are delivered orally, and break down in the stomach, releasing the micelles containing the insulin. The micelles protect the insulin from the degradative enzymes and pH in the gastric environment. The micelles travel to the small intestine, where lipases cleave the ester linkage in the hydrophilic element. The cleavage of this linker unmasks the pentavalent monosaccharide ligand, which then binds to lectins present on the apical membrane surface of mucosal enterocytes, localizing the micelles to the cells. The micelles then cross the mucosal enterocytes by receptor-mediated transcytosis induced by the binding of the ligand to the lectin, which transports the micelles to the bloodstream. Gradual decomposition of the micelles, initiated by cleavage of the hydrophilic element, results in the release of insulin into the bloodstream.

Example 16

Oral Delivery of Insulin Via the Transcellular Route

This example is the same as Example 15, except that the hydrophobic element of the smart surfactant is comprised of a steroidal sapogenin. The hydrophilic element is comprised of an oligosaccharide, which contains a cleavable linker sensitive to pH 7.5, such that it is cleaved in the small intestine to unmask a positively-charged group. Cleavage at this location also generates a permeation enhancing agent comprising a sapogenin linked to an oligosaccharide. The micelles are formed in the presence of a protease inhibitor, such that the protease inhibitor is incorporated into the core of the polar-core micelles that are formed. The formulation and administration process is as described in Example 15. Upon reaching the small intestine, the alkaline pH of the intestinal environment causes the cleavage of the linker in the hydrophilic element, unmasking a positively-charged group, which results in the adhesion of the micelles to the mucin layer of the intestinal enterocytes. The cleavage event also causes the micelles to break down into individual molecules of a permeation enhancer linked to the insulin. The linker from the PLE to the insulin is cleaved in the alkaline environment, and the permeation enhancer allows the insulin and the protease inhibitor to enter the mucosal enterocytes via the apical membrane. The protease inhibitor prevents proteases within the enterocytes from degrading the insulin, which is then able to cross the basolateral membrane of the enterocytes due to the presence of the permeation enhancer and enter the bloodstream.

Example 17

Oral Delivery of Insulin Via the Paracellular Route

This example is the same as Example 15, except that the hydrophilic element of the smart surfactant contains a linkage that is cleaved by lipases to unmask groups containing multivalent positively-charged groups at the end of each hydrophilic element. The polar-core micelles are formed such that they contain a protease inhibitor in the core as well as insulin. The micelles are formulated and delivered orally as described in Example 15. Once the micelles reach the small intestine, lipases cleave the linkage in the hydrophilic element, unmasking the multivalent positively-charged groups. The unmasking of the positively-charged groups causes the micelles to bind to the mucin layer of the intestinal enterocytes, and also creates gaps between the enterocytes at the location of their tight junctions with each other. Cleavage of the hydrophilic element also causes the micelle to decompose, releasing the protease inhibitor. Exposure of the linkage between the insulin and the PLE to alkaline intestinal pH causes the linkage to cleave and release insulin. The protease inhibitor inhibits any protease activity present, and the insulin travels via the paracellular route into the bloodstream.

Example 18

Oral Delivery of Erythropoietin

EPO protected with hydrophilic copolymers as in Example 10, is incorporated into polar-core micelles using a smart surfactant. The PLE of the smart surfactant bears groups with a charge opposite to the net charge of EPO at pH 7. The hydrophilic element of the smart surfactant contains a linkage cleavable at the alkaline pH present in the small intestine, such that a pentavalent monosaccharide ligand for a lectin present on the surface of enterocytes in the intestinal mucosa is unmasked. Cleavage of the linker will also result in the gradual decomposition of the micelle to release the protected EPO. The protected EPO is added to a buffered aqueous solution of the smart surfactant, and gentle agitation is applied to generate a nearly monodisperse population of polar-core micelles containing protected EPO at their core. Dextrin is added to the micellar suspension, which is then lyophilized to produce a powder with a long shelf life. The powder is formulated into tablets, which are administered orally. The tablets break down in the stomach, releasing the micelles containing the protected EPO. The EPO is protected from the degradative enzymes and low pH of the gastric environment by the micellar structure. The micelles travel to the small intestine, where cleavage of the linker in the hydrophilic element occurs due to the alkaline pH of the intestinal environment. The cleavage results in the unmasking of the pentavalent monosaccharide ligand, which then binds to lectins present on the surface of intestinal enterocytes. Binding of the ligand induces receptor-mediated transcytosis, which transports the micelles to the bloodstream. Gradual decomposition of the micelles due to the cleavage of the linker in the hydrophilic element releases the protected EPO into the bloodstream.

Example 19

Oral Delivery of HCV E2 Protein to the Lymphatic System for the Generation of Immune Protection Hepatitis C virus E2 protein is encapsulated in a polar-core micelle formed with a smart surfactant. The smart surfactant contains a PLE bearing groups with a charge opposite to the net charge of E2 protein at pH 7. The hydrophilic element contains a linker cleavable by lipases in the small intestine, such that positively-charged groups are unmasked. The E2 protein and an adjuvant are added to a buffered aqueous solution at pH 7 containing the smart surfactant. With gentle agitation, polar-core micelles containing E2 protein and the adjuvant in the core are produced. The micelles are nearly monodisperse, and are about 50 nm in average diameter. Glucose is added to the suspension of micelles, and the suspension is lyophilized to produce a powder with a suitable shelf life. The powder is formulated into tablets, which are administered orally. The tablets break down in the stomach to release the micelles, which protect the E2 protein contained inside from the degradative enzymes and low pH of the gastric environment. The micelles travel to the small intestine, where lipases cleave the linkage in the hydrophilic element of the smart surfactant, causing positively-charged groups to be unmasked. The unmasked positively-charged groups cause the micelles to adhere to the mucin layer of the intestinal wall. The particles are taken up by the M-cells of Peyer's patches due to their size, and are transported to the lymphatic system by transcytosis. Gradual breakdown of the micelles, initiated by cleavage of the linkage in the hydrophilic element by lipases, results in the release of the E2 protein contained within into the lymph. The presence of the E2 protein in the lymph results in an immune response that induces protective immunity to Hepatitis C virus infection.

Example 20

Oral Delivery of a Hydrophobic Small Molecule Drug to the Bloodstream Via the Stomach A hydrophobic small molecule drug "P" lacks oral bioavailability due to its low solubility in aqueous media. A smart surfactant for the delivery of hydrophobic molecules is synthesized containing a linkage within the hydrophilic element sensitive to a pH of less than 3. The hydrophobic element is the drug itself. Drug P is added to a buffered aqueous solution at pH 7.5 containing the smart surfactant. The mixture is agitated mechanically to generate a nearly monodisperse suspension of smart micelles containing drug P at their core. Glucose is added to the suspension, and it is then lyophilized to produce a powder with an adequate shelf life, and which can be formulated into tablets. The drug is administered orally in tablet form and the tablet breaks down in the stomach to release the micellar emulsion. The breakdown of the hydrophilic element of the surfactant due to cleavage of the labile linkage in the hydrophilic element at the low pH present in the gastric environment causes the micelle to decompose, and drug P to be released. Drug P permeates the epithelial layer of the stomach wall, and enters the bloodstream.

Example 21

Intravenous Delivery of an Artificial Chromosome to Bone Marrow Stem Cells

A smart surfactant for the formation of polar-core micelles is synthesized, in which the PLE contains chemical groups, which are positively charged at pH 7.5. Within the hydrophilic element is a peptidic nuclear localization sequence (NLS) in masked form, and at the free end of the hydrophilic element a ligand is attached that binds to receptors on bone marrow stem cells. An artificial chromosome containing a functional copy of the human adenosine deaminase (ADA) gene is added to a buffered aqueous solution of the smart surfactant at pH 7.5, and the mixture is agitated to generate a suspension of nearly monodisperse polar-core micelles of an average diameter of 50 nm containing the artificial chromosome at their core. Glucose is added to this suspension, and the mixture is lyophilized to generate a powder with an acceptable shelf life. Immediately prior to administration, the powder is resuspended in sterile PBS pH 7.5, and then administered intravenously to a patient with ADA deficiency. The micelles containing the artificial chromosome circulate in the bloodstream, and travel to the bone marrow, where the ligand binds to receptors on the surface of bone marrow stem cells. The micelles are transported inside the cells by receptor-mediated endocytosis. The micellar coating protects the artificial chromosome from damage by the low pH, oxidizing conditions, and enzymatic activities present in the endosomes. Upon reaching the cytoplasm, reduction of a disulfide linkage in the hydrophilic element of the smart surfactant unmasks the NLS, which then causes the micelle to be transported through pores in the nuclear membrane into the nucleus. Gradual decomposition of the micelle, initiated by reduction of the disulfide linkage, causes the artificial chromosome to be released into the nuclear environment, allowing expression of the ADA gene.

Example 22

Oral Delivery of an Antiviral Ribozyme to HCV Infected Liver Cells

A smart surfactant for the formation of polar-core micelles is synthesized in which the PLE contains chemical groups, which are positively charged at pH 5. At the free end of the hydrophilic element a pentavalent galactose ligand is attached, and within the hydrophilic element is contained a disulfide linkage. A ribozyme capable of site-specifically cleaving HCV RNA is added to an aqueous buffer at pH 5 containing the smart surfactant, and the mixture is agitated to generate a nearly monodisperse suspension of polar-core micelles of 30 nm average diameter containing the ribozyme at their core. Mannan is added to the suspension, and the mixture is lyophilized to produce a powder with an acceptable shelf life. The powder is formulated into tablets, which are administered orally to patients infected with HCV. In the stomach, the tablet breaks down, releasing the micelles into the gastric fluid. The micelles protect the encapsulated ribozyme from degradation due to the low pH of the stomach and alkaline pH of the small intestine, as well as digestive enzymes. The micelles travel to the small intestine, where they are absorbed due to their small size, and are transported via transcytosis to the bloodstream. The micelles circulate in the bloodstream to the liver, where the galactose ligand interacts with liver cell receptors for galactose, resulting in receptor-mediated endocytosis of the micelles. The micellar structure protects the encapsulated ribozyme from degradation due to conditions (low pH, enzymatic activity, oxidative conditions) in the endosome. Upon arriving in the cytoplasm, the disulfide in the hydrophilic element is reduced, resulting in cleavage of the hydrophilic element, and uncoating of the micelle, thereby releasing the ribozyme into the cytoplasm. The ribozyme is then able to site-specifically cleave conserved sequences of HCV RNA present in the cell, eliminating the virus.

We claim:

1. A surfactant comprising a hydrophobic element having a log P value greater than 0 covalently attached to a hydrophilic element, wherein said hydrophobic element has a molecular weight of between about 10-2000 daltons, and wherein said surfactant is capable of forming a micelle that encapsulates a hydrophobic drug, said micelle having a core comprising said hydrophobic drug, wherein said core is substantially free of said hydrophobic element, said hydrophobic element comprising less than about 50% of a total weight of the core, and wherein said hydrophilic element comprises linkers that are capable of being cleaved under physiological conditions, and said linkers being capable of generating a permeation-enhancing molecule.

2. A surfactant comprising a hydrophobic element having a log P value greater than 0 covalently attached to a hydrophilic element, wherein said hydrophobic element has a molecular weight of between about 10-2000 daltons, and wherein said surfactant is capable of forming a micelle that encapsulates a hydrophobic drug, said micelle having a core comprising said hydrophobic drug, wherein said core is substantially free of said hydrophobic element, said hydrophobic element comprising less than about 50% of a total weight of the core, and wherein said hydrophilic element comprises linkers that are capable of being cleaved under physiological conditions, and said linkers being capable of unmasking an element selected from the group consisting of binding elements and transport elements.

3. The surfactant of claim 2 wherein said binding elements are selected from the group consisting of ligands, bioadhesive functional groups, and mixtures thereof.

4. The surfactant of claim 2 wherein said transport elements are selected from the group consisting of nuclear localization sequences, membrane-traversing molecules, and mixtures thereof.

5. A micelle for encapsulating a hydrophobic drug comprising a plurality of surfactants, said plurality of surfactants comprising a hydrophobic element having a log P value greater than 0 covalently attached to a hydrophilic element, wherein said hydrophobic element has a molecular weight of between about 10-2000 daltons, said micelle having a core comprising said hydrophobic drug, wherein said core is substantially free of said hydrophobic element, and wherein said hydrophobic element comprises less than about 50% of a total weight of the core.

6. The micelle of claim 5 wherein said micelle comprises a large volume of said hydrophobic drug.

7. The micelle of claim 5 wherein said hydrophobic element is a small molecule or an oligomer or polymer.

8. The micelle of claim 7 wherein said oligomer or polymer has a single chain length.

9. The micelle of claim 7 wherein said oligomer or polymer has a narrow distribution of chain lengths.

10. The micelle of claim 7 wherein said oligomer or polymer is selected from the group consisting of peptides having hydrophobic side chains and unnatural stepwise oligomers having hydrophobic side chains.

11. The micelle of claim 10 wherein said unnatural stepwise oligomers are selected from the group consisting of peptoids, oligocarbamates, oligoureas, and mixtures thereof.

12. The micelle of claim 7 wherein said oligomer or polymer is a short peptide comprising less than about 20 amino acids.

13. The micelle of claim 12 wherein said short peptide comprises from 2 to about 20 amino acids.

14. The micelle of claim 13 wherein said short peptide comprises from 2 to about 15 amino acids.

15. The micelle of claim 14 wherein said short peptide comprises from 2 to about 10 amino acids.

16. The micelle of claim 15 wherein said short peptide comprises from 2 to about 5 amino acids.

17. The micelle of claim 7 wherein said small molecule is said hydrophobic drug or an analog thereof.

18. The micelle of claim 7 wherein said small molecule is selected from the group consisting of cholesterol, cholesterol derivatives, bile acids, bile acid derivatives, steroidal sapogenins, triterpenoid sapogenins, steroidal sapogenin derivatives, triterpenoid sapogenin derivatives, steroid derivatives, amino acids, and mixtures thereof.

19. The micelle of claim 18 wherein said amino acid is an aromatic amino acid.

20. The micelle of claim 5 wherein said hydrophilic element is an oligomer or polymer.

21. The micelle of claim 20 wherein said oligomer or polymer has a single chain length.

22. The micelle of claim 20 wherein said oligomer or polymer has a narrow distribution of chain lengths.

23. The micelle of claim 20 wherein said oligomer or polymer has a linear, branched, or cyclic structure, and/or includes side chains of gradually increasing size to generate a cone-like shape.

24. The micelle of claim 20 wherein said oligomer or polymer is selected from the group consisting of oligosaccharides, polysaccharides, peptides, unnatural stepwise oligomers, and mixtures thereof.

25. The micelle of claim 24 wherein said unnatural stepwise oligomers are selected from the group consisting of peptoids, oligocarbamates, oligoureas, and mixtures thereof.

26. The micelle of claim 5 wherein said hydrophilic element further comprises at least one binding element.

27. The micelle of claim 26 wherein said binding element is selected from the group consisting of ligands, bio adhesive functional groups, and mixtures thereof.

28. The micelle of claim 5 wherein said hydrophilic element further comprises at least one transport element.

29. The micelle of claim 28 wherein said transport element is selected from the group consisting of nuclear localization sequences, membrane-traversing molecules, and mixtures thereof.

30. The micelle of claim 5 wherein said hydrophilic element further comprises linkers that are capable of being cleaved under physiological conditions.

31. The micelle of claim 30 wherein said linkers comprise amides, carbamates, thiocarbamates, oxygen esters, thioesters, glycolate esters, lactate esters, orthoesters, acetals, ketals, phosphodiesters, disulfides, and mixtures thereof.

32. The micelle of claim 30 wherein said linkers are capable of destabilizing said micelle, whereby a plurality of said surfactants are shed from said core and said hydrophobic drug is exposed to an external environment.

33. The micelle of claim 30 wherein said linkers are capable of generating a permeation-enhancing molecule.

34. The micelle of claim 30 wherein said linkers are capable of unmasking an element selected from the group consisting of binding elements and transport elements.

35. The micelle of claim 34 wherein said binding elements are selected from the group consisting of ligands, bioadhesive functional groups, and mixtures thereof.

36. The micelle of claim 34 wherein said transport elements are selected from the group consisting of nuclear localization sequences, membrane-traversing molecules, and mixtures thereof.

37. The micelle of claim 5 wherein said surfactant is a permeation-enhancing molecule.

38. The micelle of claim 5 wherein said surfactant and its physiological breakdown products are non-toxic, non-immunogenic, and readily excretable.

39. The micelle of claim 5 wherein said micelle further comprises a molecule selected from the group consisting of permeation enhancing molecules, inhibitors of undesirable enzymatic activities, and mixtures thereof.

40. The micelle of claim 5 wherein said micelle is formed by a self-assembly process.

41. The micelle of claim 5 formed by a method comprising dissolving said hydrophobic drug in a volatile solvent or FDA-approved oil and adding the dissolved hydrophobic drug to an aqueous solution comprising said surfactant, thereby forming micelles.

42. The micelle of claim 5 wherein said micelles have a hydrodynamic diameter in the range of from about 1 to about 100 nm.

43. The micelle of claim 42 wherein said range is of from about 5 to about 80 nm.

44. The micelle of claim 5 wherein said covalent attachment is noncleavable or cleavable under physiological conditions.

* * * * *